(12) United States Patent
Odom John et al.

(10) Patent No.: US 11,925,455 B2
(45) Date of Patent: Mar. 12, 2024

(54) METHODS FOR DIAGNOSING MALARIA

(71) Applicant: Washington University, St. Louis, MO (US)

(72) Inventors: Audrey Odom John, St. Louis, MO (US); Chad Schaber, St. Louis, MO (US); Indi Trehan, St. Louis, MO (US); Baranidharan Raman, St. Louis, MO (US); Nalin Katta, Boston, MA (US)

(73) Assignee: Washington University, St. Louis, MO (US)

( * ) Notice: Subject to any disclaimer, the term of this patent is extended or adjusted under 35 U.S.C. 154(b) by 776 days.

(21) Appl. No.: 16/641,501

(22) PCT Filed: Aug. 27, 2018

(86) PCT No.: PCT/US2018/048146
§ 371 (c)(1),
(2) Date: Feb. 24, 2020

(87) PCT Pub. No.: WO2019/040937
PCT Pub. Date: Feb. 28, 2019

(65) Prior Publication Data
US 2021/0128016 A1 May 6, 2021

Related U.S. Application Data

(60) Provisional application No. 62/550,283, filed on Aug. 25, 2017.

(51) Int. Cl.
*A61B 5/08* (2006.01)
*A01N 27/00* (2006.01)
(Continued)

(52) U.S. Cl.
CPC ............ *A61B 5/082* (2013.01); *A01N 27/00* (2013.01); *A61B 5/7246* (2013.01); *A61B 5/7264* (2013.01); *A61B 5/7282* (2013.01); *G01N 33/497* (2013.01); *A61B 2010/0087* (2013.01); *A61B 2560/0431* (2013.01); *G01N 2033/4975* (2013.01)

(58) Field of Classification Search
CPC ..... A61B 5/082; A61B 5/7246; A61B 5/7264; A61B 5/7282; A61B 2010/0087; A61B 2560/0431; A61B 5/097; A01N 27/00; G01N 33/497; G01N 2033/4975; Y02A 50/30
See application file for complete search history.

(56) References Cited

FOREIGN PATENT DOCUMENTS

WO 2015/077843 A1 6/2015
WO WO-2015077843 A1 * 6/2015 ............ A61B 5/082

OTHER PUBLICATIONS

Berna, A.Z., et al., "Analysis of Breath Specimens for Biomarkers of Plasmodium falciparum Infection," 2015, J. Infect. Dis. 212, 1120-1128, 9 pages.
(Continued)

*Primary Examiner* — Lyle Alexander
*Assistant Examiner* — Ali Husain Faraz
(74) *Attorney, Agent, or Firm* — Stinson LLP

(57) ABSTRACT

Various methods of diagnosing and monitoring a subject infected with a *Plasmodium* parasite are described. Also, compositions and methods for attracting mosquitos are also described.

8 Claims, 10 Drawing Sheets

(51) Int. Cl.
*A61B 5/00* (2006.01)
*A61B 10/00* (2006.01)
*G01N 33/497* (2006.01)

(56) References Cited

OTHER PUBLICATIONS

Chang, Y., et al., "Detection of Volatile Organic Compounds by Self-Assembled Monolayer Coated Sensor Array with Concerntration-Independent Fingerprints," 2016, Science Reports, 6:23970, 12 pages.

Chen, C., et al., "A Wireless Hybrid Chemical Sensor for Detection of Environmental Volatile Organic Compounds," May 2013, IEEE Sens J, 13/5:1748-1755, 17 pages.

Deng, Y., et al., "A Novel Wireless Wearable Volatile Organic Compound (VOC) Monitoring Devise with Disposable Sensors," 2016, Sensor, 16:2060, 13 pages.

Gao, J., et al., "Breath Analysis for Noninvasively Differentiating Acinetobacter Baumannii Ventilator-associated Pneumonia from its Respiratory Tract Colonization of Ventilated Patients," 2016, J. Breath Res. 10/2: 027102, 14 pages.

Goyette, J., "Could a Test for Malaria be as Easy as a Breathalyzer?" Apr. 5, 2015, Science Friday, Public Radio International, downloaded http://www.pri.org/stories/2015-04-05/cou-test-malaria-be-easy-breathalyzer[6/6/20162:48:06 PM], 5 pages.

Guggisberg, A.M., et al., "A Sugar Phosphatase Regulates the Methylerythritol Phosphate (MEP) Pathway in Malaria Parasites," Jul. 2014, Nature Communications, Macmillan Publishers Ltd, DOI: 10.1038/ncomms5467, 10 pages.

Jones et al., "A Novel Fast Gas Chromatograph Method for Higher Time Resolution Measurements of Speciated Monoterpenes in Air," 2014, Atmos Meas Tech, 7:1259-1275, 17 pages.

Kelly, M., et al., "Malaria Parasites Produce Volatile Mosquito Attractants," 2015, mBio, 6/1 e00235-15, 6 pages.

Kwak, J., et al., "Evaluation of Bio-VOC Sampler for Analysis of Volatile Organic Compounds in Exhales Breath," 2014, Metabolites, 4:879-888, 10 pages.

Mochalski, P., et al., "Blood and Breath Levels of Selected Volatile Organic Compounds in Healthy Volunteers," 2013, Analyst, 138:2134-45, 12 pages.

O'Hara, M.E., et al., "Limonene in Exhaled Breath is Elevated in Hepatic Encephalophy," 2016, J. Breath Res, 10/4, 11 pages.

Pereira, J., et al., Breath Analysis as a Potential and Non-Invasive Frontier in Disease Diagnosis: An Overview, 2015, Metabolites, 5/3-55, 53 pages.

Schmidt, K., et al., "Current Challenges in Volatile Organic Compounds Analysis as Potential Biomarkers of Cancer," J Biomarkers, vol. 2015, Art ID 981458, 17 pages.

Van den Dool, H., "A Generalization of the Retention Index System Including Linear Temperature Programmed Gas-Liquid Partition Chromatography," 1963, J. Chromatogr, 11:463-471, Abstract only, 1 page.

Wong, P.M., et al., "Investigation of Volatile Organic Biomarkers Derived from Plasmodium falciparum in vitro," 2012, Malaria J., 11:314-321, 8 pages.

Wenig, P., et al., "OpenChrom: A Cross-Platform Open Source Software for the Mass Spectrometric Analysis of Chromatographic Data," 2010, BMC Bioinformatics, 11:405, 9 pages.

"Malaria-Infected Cells Produce Odors Attractive to Mosquitoes," Mar. 24, 2015, Phys Org, Am Soc Microbiol, https://phys.org/news/2015-03-malaria-infected-cells-odors-mosquitoes.html.

Guidelines for the Treatment of Malaria, 3rd Ed., 2015, World Health Organization ISBN 978 92 4 154912 7, 317 pages.

International Search Report and Written Opinion issued in PCT/US2018/048146, dated Dec. 3, 2018, 11 pages.

International Preliminary Report on Patentability issued in PCT/US2018/048146, dated Mar. 5, 2020, 8 pages.

\* cited by examiner

METHODS FOR DIAGNOSING MALARIA

REFERENCE TO RELATED APPLICATIONS

This application is the 371 National Stage Application based on International Application Serial No. PCT/US2018/048146, filed Aug. 27, 2018, and claims the benefit of U.S. Provisional Application Ser. No. 62/550,283, filed Aug. 25, 2017, the contents of which are incorporated by reference herein.

FIELD OF THE INVENTION

The present invention relates to various methods of diagnosing and monitoring a subject infected with a *Plasmodium* parasite. The present invention further relates to compositions and methods for attracting mosquitos.

BACKGROUND OF THE INVENTION

Malaria remains a major threat to global health with over 250 million cases per year and one million deaths per year, primarily in children under the age of five. Malaria is transmitted through the bite of *Anopheles gambiae* (mosquitoes) and is diagnosed by positive identification of parasites (commonly *Plasmodium falciparum* or *P. vivax*) in a subject's blood using stained blood film or similar technology. In developing regions like sub-Saharan Africa, where malaria vectors and infection rates are high, the lack of proper infrastructure and instrumentation leads to pre-emptive treatment of a supposed malarial infection with anti-malaria medications, without verifying that an infection exists. This, in turn, has led to parasitic resistance against the common therapeutics available. Therefore, a need exists for an inexpensive and convenient diagnostic strategy for malaria that can be easily and accurately employed in various locations.

BRIEF SUMMARY OF THE INVENTION

In various aspects the present invention relates to methods of diagnosing or monitoring a subject infected with a *Plasmodium* parasite such *Plasmodium falciparum* or *Plasmodium vivax*. Additional embodiments are directed to detection of various volatile organic chemicals in exhaled breath or condensate breath samples. Still further embodiments are directed to compositions useful as mosquito attractants and methods for attracting mosquitoes.

Various methods for diagnosing a *Plasmodium* infection in an individual comprise analyzing a sample of exhaled breath or condensate breath for at least one monoterpene wherein the concentration of the monoterpene indicates a *Plasmodium* parasite infection. Further methods for diagnosing a *Plasmodium* infection in an individual comprise analyzing a sample of exhaled breath or condensate breath for a series of volatile organic chemicals (VOCs) wherein the cumulative abundance of the series of VOCs indicates a *Plasmodium* parasite infection.

Additional methods of the invention include the detection of monoterpenes in exhaled breath or condensate breath from a subject wherein the monoterpenes are α-pinene, 3-carene or combinations thereof. Still further methods of the invention include the detection of a series of volatile organic chemicals in the breath or condensate breath of a subject wherein the series of VOCs comprise isoprene, nonanal, tridecane and other compounds described herein.

The present invention is also directed to methods of treating subjects diagnosed with a *Plasmodium* infection using the methods herein with therapeutically effective amounts of at least one compound effective against a *Plasmodium* parasite infection.

The present invention is also directed to mosquito attractant compositions comprising a matrix and at least one attractant compound selected from the group consisting of α-pinene, 3-carene, and combination thereof. The present invention is also directed to methods of attracting mosquitoes comprising emitting from a trap or system at least one attractant compound selected from the group consisting of α-pinene, 3-carene, and combination thereof.

Other objects and features will be in part apparent and in part pointed out hereafter.

Red numbers label the peaks of the six VOCs with largest absolute correlations to malaria status.

Figure 4A:
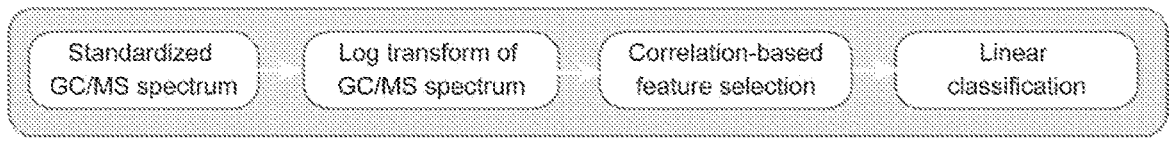
FIG. 4A is a flow chart depicting the four major steps taken to classify individuals as malaria positive or negative.
Figure 4B:
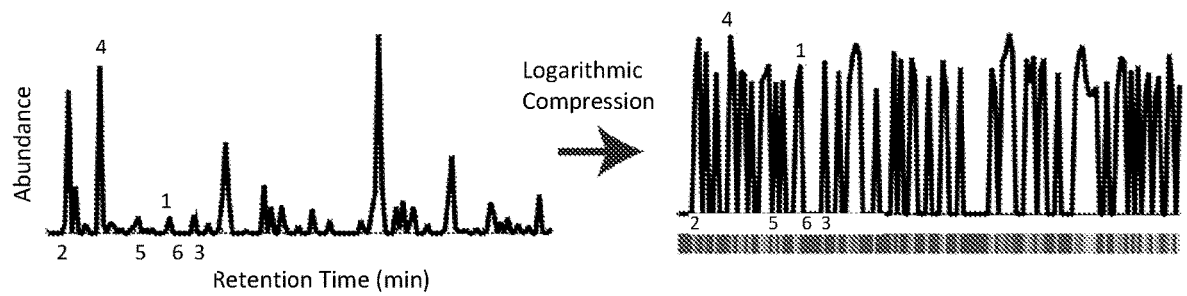
FIG. 4B shows a representative GC/MS total ion chromatograph (to the left) and the same spectrum after logarithmic compression (to the right). For visualization the abundance of each volatile organic chemical (VOC) is represented as a color bar below the compressed spectrum.
Figure 4C:
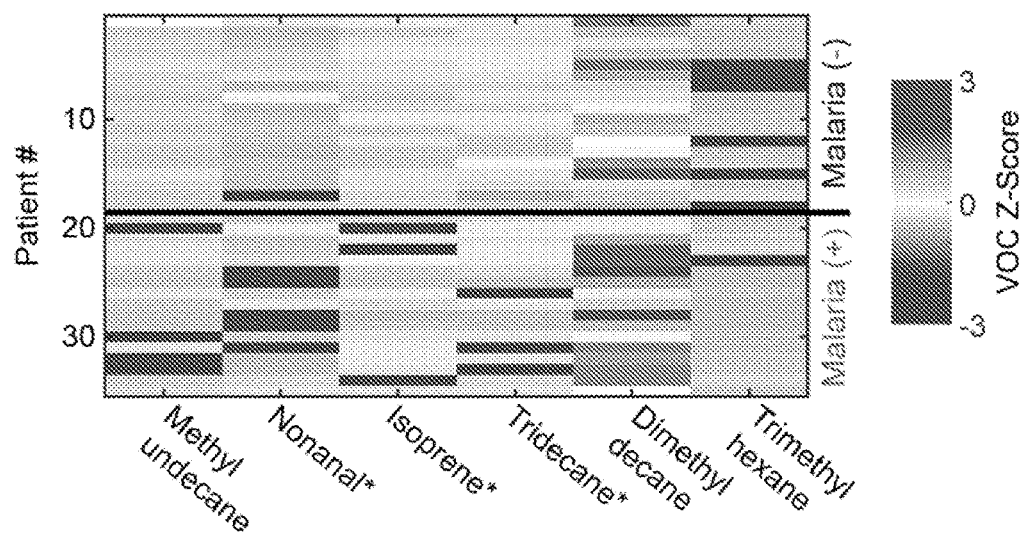

FIG. 4C is a heat map of the z-scores for the six VOCs with highest absolute correlation with malaria infection status in the patient population. Rows represent individual patients divided by malaria status above and below the solid black line. Each column represents a separate VOC. Red indicates lowered levels (negative z-scores) relative to mean and purple indicates higher levels (positive z-scores) relative to mean.

Figure 4D:
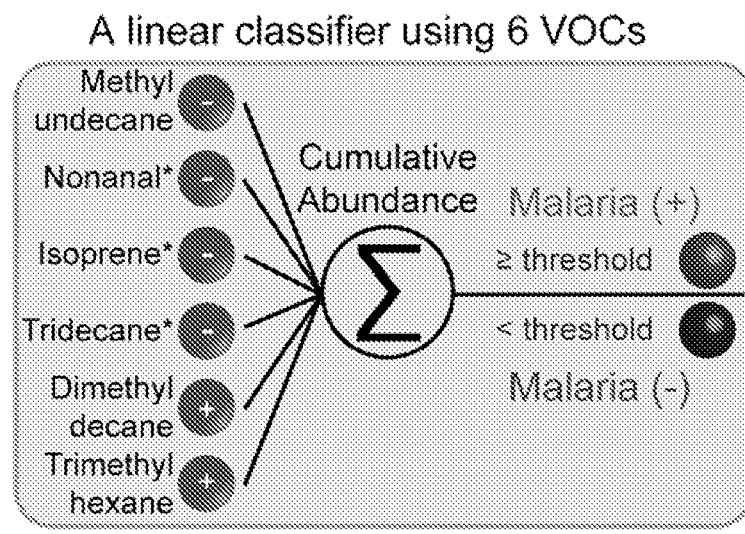

FIG. 4D is a schematic describing the classification approach. Abundances of six VOCs are linearly combined (negatively correlated VOCs are subtracted) to yield a cumulative abundance which is compared to a threshold to classify a patient as malaria positive or negative.

Figure 4E:
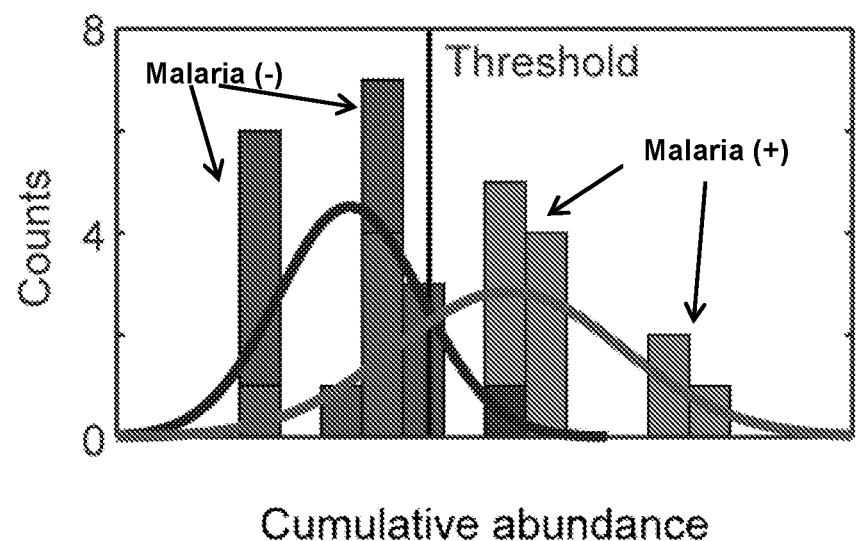

FIG. 4E is a histogram depicting the distribution of cumulative abundance of the six VOCs from children with (red) or without (blue) malaria. Overlaid curves are Gaussian distributions fitted to the two classes and which define the threshold (black line).

Figure 4F:
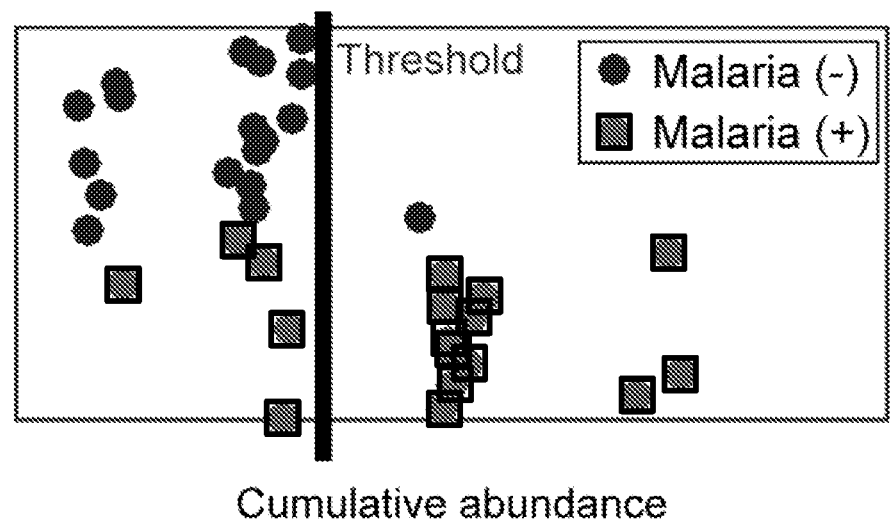

FIG. 4F is a scatterplot depicting the cumulative abundance of the six VOCs in the patient population. Data points are colored red for malaria positive individuals and blue for malaria negative patients.

Figure 4G:
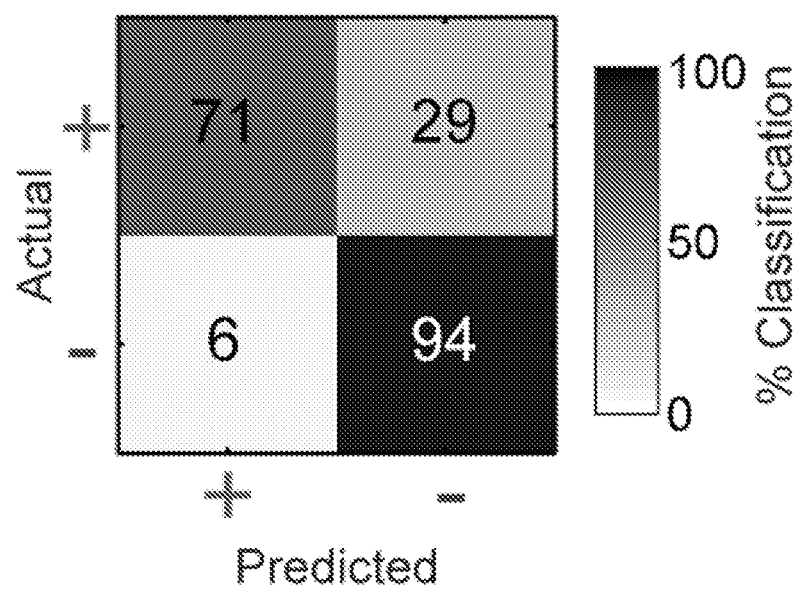

FIG. 4G is a confusion matrix of actual and predicted malaria infections status. The percentages of patients in each class are displayed.

Figure 5A:
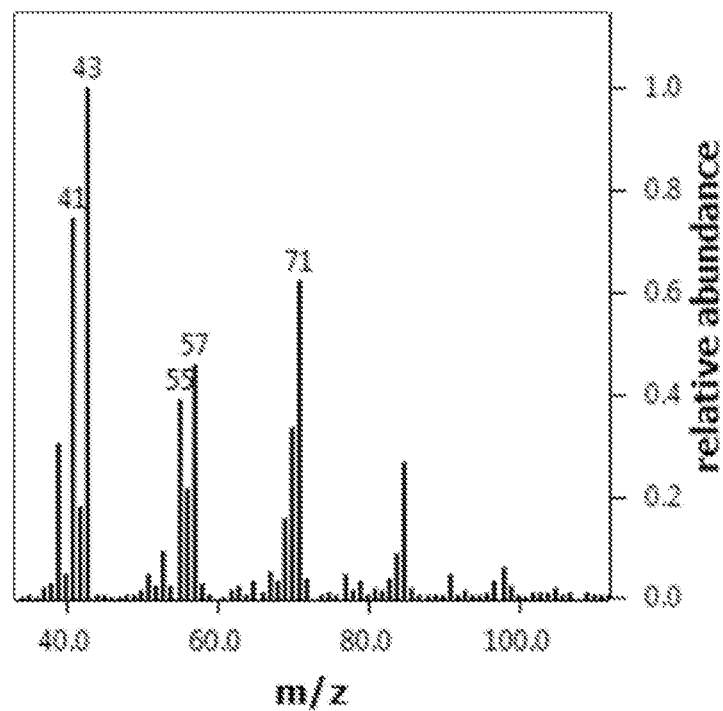

FIG. 5A is a representative spectra of 4-methyl undecane from a patient sample.

Figure 5B:
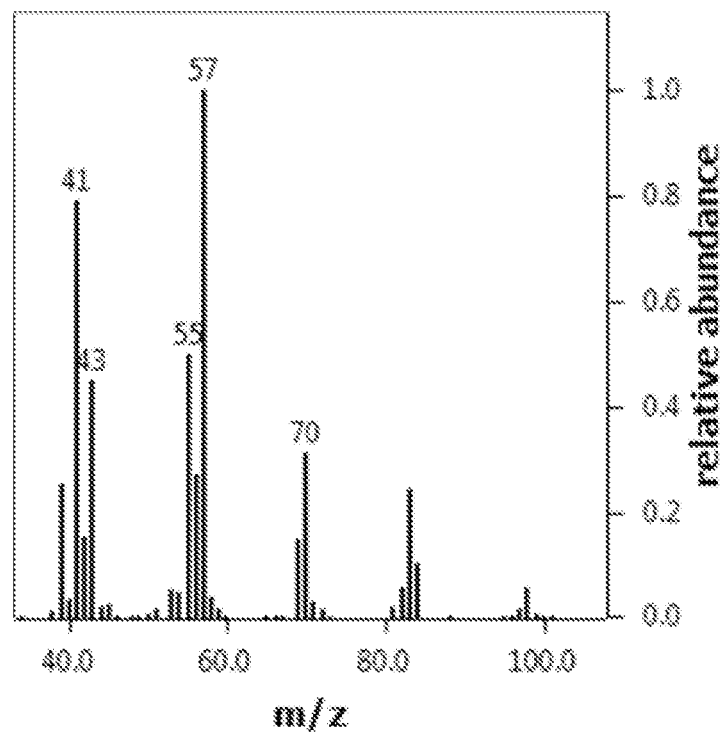

FIG. 5B is a representative spectrum of 3,7-dimethyl decane from a patient sample.

Figure 5C:
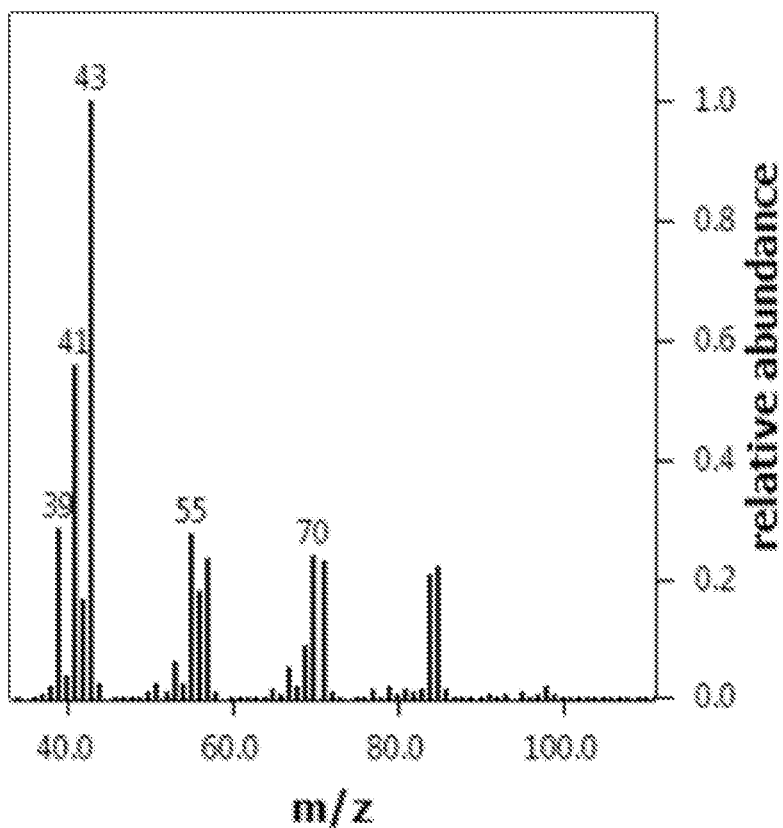

FIG. 5C is a representative spectrum of 2,3,4-trimethyl hexane from a patient sample.

DETAILED DESCRIPTION OF THE INVENTION

In various aspects, the present invention is directed to various methods of diagnosing and monitoring a subject infected with a *Plasmodium* parasite (i.e., malaria). Various methods of the present invention comprise the detection of particular volatile organic compounds from the subject, wherein the concentration of the compound(s) indicates a *Plasmodium* parasite infection. Additional aspects of the invention are directed to methods of detecting monoterpenes or particular volatile organic compounds in a subject. Further embodiments are directed to mosquito attractants.

Isoprenoids represent a diverse family of over 35,000 natural products, including sterols and terpenes. The biosynthesis of isoprenoids occurs through the repeated condensation of a key precursor, isopentenyl pyrophosphate (IPP). Mammals and fungi derive IPP from a coenzyme A (CoA)-dependent pathway, which proceeds through the key intermediate melavonate. Recent studies have identified the MEP pathway (also known as the non-melavonate and the 1-deoxy-d-xylulose 5-phosphate (DOXP) pathway) as an alternative biosynthetic route to IPP. The MEP pathway is used by plants, algae, bacteria and protozoa, but is crucially absent in mammalian systems which use the melavonate pathway to synthesize IPP. MEP pathway enzymes are known to be present in all intraerythrocytic stages of the *P. falciparum* parasite.

Subsets of isoprenoids, monoterpenes, are volatile organic chemicals (VOCs) synthesized by the MEP pathway in plants. These VOCs serve to attract nearby pollinators or insects, including *A. gambiae*. Studies have shown that *P. falciparum* infection induces monoterpene release capable of attracting *A. gambiae*. It has been discovered that these monoterpenes could serve to attract mosquitoes to *Plasmodium* infected individuals to ensure further propagation of the parasite, and that these monoterpenes may also be used as biomarkers in subject samples. It has been further discovered that elevated levels of monoterpenes as well as changes in the concentration of certain other volatile organic compounds (VOCs) as described herein can be found in the breath of malaria patients. It has been also been discovered that the breath of malaria patients exhibits certain changes in the concentration of other volatile organic compounds (VOCs) as described herein. In view of these discoveries, various methods described herein include analyzing a sample of exhaled breath or condensate breath obtained from the subject for one or more monoterpenes and/or the VOCs described herein.

Various methods of the present invention include methods for diagnosing or monitoring a subject with a *Plasmodium* parasite infection (malaria). In some embodiments, the methods comprise analyzing a sample of exhaled breath or condensate breath obtained from the subject for at least one monoterpene, wherein the concentration of the monoterpene indicates a *Plasmodium* parasite infection. Typically, the *Plasmodium* parasite infection is an infection of *Plasmodium falciparum* or *Plasmodium vivax*.

In various embodiments, the sample is analyzed for at least one compound selected from the group consisting of α-pinene, 3-carene, and combinations thereof. In some embodiments, the sample is analyzed for α-pinene and 3-carene. In certain embodiments, the sample is analyzed for a monoterpene comprising α-pinene.

In various embodiments, methods for analyzing a sample of exhaled breath or condensate breath obtained from a subject can include the use of at least one technique selected from the group consisting of photo ionization detection, flame ionization detection, gas chromatography-mass spectrometry (GC-MS), proton transfer reaction mass spectrometry (PTR-MS), colorimetry, infrared spectroscopy, electrochemical fuel cell sensing, semiconductor gas sensing, quartz tuning fork (QTF) sensors, electronic noses and combinations thereof. These methods are described in more detail herein.

In various embodiments, the method comprises use of an electronic nose, or any microarray capable of sensing multiple volatile signatures, particularly one calibrated to the detection of volatile organic compounds (Chang et al., Science Reports, 6(2016): 23970). In further embodiments, the method comprises use of a portable wireless volatile organic compound monitoring device that employs quartz tuning fork (QTF) sensors (Deng et al., *Sensors* 2016, 16(12), 2060). These techniques involve adsorption of VOCs onto modified (coated) QTFs which alters their resonance frequency and enables quantification of VOC concentration.

The analysis described for the methods herein could also include use of a portable device comprising a sample collection and pre-concentration unit, a sample separation column, and a sensitive, selective and fast sensor (IEEE Sens J. 2013 May; 13(5):1748-1755).

In some embodiments, the method further comprises the use of solid-phase micro-extraction fibers to extract and concentrate volatile chemicals in exhaled breath for further analysis. For example, various methods can include the use of micro-extraction fibers alongside GC-MS to detect monoterpenes in exhaled breath of human patients (Gao et al., J. Breath Res. 10:2 (2016) 027102). In further embodiments, the method comprises use of PTR mass spectrometry to detect monoterpenes in collected breath of subjects (O'Hara et al., J. Breath Res. 10:4 (2016)). PTR mass spectrometry uses gas phase hydronium ($H_3O+$) ions to ionize trace VOCs in an air sample in order to detect and identify them using mass spectrometry. In still other embodiments, the method comprises use of fast gas chromatography-flame ionization detection (Fast-GC-FID) which is known in the art to detect monoterpenes in ambient air samples (Jones et al., Atmos. Meas. Tech, 7, 1259-1275, 2014). Briefly, this method involves separating volatile chemicals on a gas column and using a hydrogen flame to oxidize them for detection.

In various embodiments, the analysis of the at least one monoterpene is conducted using a portable, hand-held breathalyzer or electronic nose device. The technique or device used for analysis can also include a display or be in communication with a further device (e.g., monitor or printer) that displays the results of the analysis.

Further the methods for diagnosing or monitoring a subject with a *Plasmodium* parasite infection (malaria) comprise analyzing a sample of exhaled breath or condensate breath obtained from the subject for a series of volatile organic compounds (VOCs) comprising: isoprene, nonanal, tridecane, 4-methyl undecane (i.e., Compound A having a base ion peak mass-to-charge (m/z) ratio of 43 and a retention time of about 14.52 minutes as determined by gas chromatography-mass spectrometry (GC-MS)), 3,7-dimethyl decane (i.e., Compound B having a base ion peak m/z ratio of 57 and a retention time of about 11.83 minutes as determined by GC-MS), and 2,3,4-trimethyl hexane (Compound C, having a base ion peak m/z ratio of 43 and a retention time of about 6.27 minutes as determined by GC-MS); determining a concentration for each of the VOCs; and calculating a cumulative abundance based on the concentrations for the VOCs, wherein the cumulative abundance indicates a *Plasmodium* parasite infection. GC-MS parameters used for the analysis of Compounds A, B, and C are further specified in Example 1.

Without being bound by theory, the spectrum obtained for Compound A is consistent with that for 4-methyl undecane. Further, the spectrum obtained for Compound B is consistent with that for 3,7-dimethyl decane. Also, the spectrum obtained for Compound C is consistent with that for 2,3,4-trimethyl hexane. Representative spectra of Compounds A, B, and C are provided in FIGS. 5A-5C, respectively, for reference.

The cumulative abundance is calculated by adding the concentrations of 3,7-dimethyl decane (i.e., Compound B) to the concentration of 2,3,4 trimethyl hexane (i.e., Compound C) and then subtracting the sum concentrations of isoprene, nonanal, tridecane, and 4-methyl undecane (i.e., Compound A). In this way, samples with elevated levels of 3,7-dimethyl decane and 2,3,4 trimethyl hexane alongside lowered levels of isoprene, nonanal, tridecane, and 4-methyl undecane will produce a cumulative abundance greater than baseline samples.

In various embodiments, reduced levels of isoprene, nonanal, tridecane and 4-methyl undecane correspond to a *Plasmodium* infection. In some embodiments, elevated levels of 3,7-dimethyl decane and 2,3,4-trimethyl hexane correspond to a *Plasmodium* infection. In further embodiments, reduced levels of isoprene, nonanal, tridecane and 4-methyl undecane and elevated levels of 3,7-dimethyl decane and 2,3,4-trimethyl hexane correspond to a *Plasmodium* infection. In certain embodiments, concentrations of the series of VOCs in a subject are compared to concentrations in a healthy individual.

In various embodiments, the method of diagnosing or monitoring a *Plasmodium* infection in a subject comprises analyzing a sample of breath or condensate breath for the series of volatile organic chemicals using at least one technique selected from the group consisting of photo ionization detection, flame ionization detection, gas chromatography—mass spectrometry (GC-MS), proton transfer reaction mass spectrometry (PTR-MS), colorimetry, infrared spectroscopy, electrochemical fuel cell sensing, semiconductor gas sensing, quartz tuning fork (QTF) sensors, electronic noses and combinations thereof.

In further embodiments, the analysis of the series of VOCs is conducted using a portable, hand-held breathalyzer device.

In additional embodiments, the methods of diagnosing or monitoring a *Plasmodium* infection can comprise the combination of any of the methods described herein. Specifically, one embodiment of the invention comprises combining the detection of a monoterpene with detection of the series of VOCs and diagnosing or monitoring the *Plasmodium* infection using the levels of monoterpenes and the series of VOCs in the breath of the subject.

In some embodiments of the present invention, the methods of diagnosing or monitoring a *Plasmodium* infection by analyzing breath samples for monoterpenes and/or the series of VOCs can further comprise analyzing the same sample for one or more volatile organic chemicals selected from the group consisting of allyl methyl sulfide, 1-methylthopropane, (E)-1-methylthio-1-propene, (Z)-1-methylthio-1-propene, and combinations thereof. WO2015/077843, which is hereby incorporated by reference, describes the detection of these compounds to aid in the diagnosis and monitoring of *Plasmodium* infections. The current invention is directed towards augmenting their diagnostic power with the simultaneous detection of monoterpenes and/or the series of VOCs described herein. Analyzing for a combination of biomarkers of the *Plasmodium* parasite infection can enhance the effectiveness and accuracy of the diagnostic/monitoring methods described herein.

In various embodiments of diagnosis and monitoring of subjects using the methods described herein, samples from the subjects can be exhaled breath or condensate breath. In various embodiments, the sample obtained from the subject is exhaled breath. In some embodiments, the method further comprises condensing or concentrating the sample before analysis.

In various embodiments, the concentration of the monoterpene or the series of VOCs in breath or breath condensate aids in the diagnosis or the monitoring of a *Plasmodium* infection. In some embodiments, the concentration of the monoterpene or the compounds in the series of VOCs in the breath or breath condensate is compared to levels of monoterpene or levels of the series of VOCs in the breath of other subjects determined to be free of *Plasmodium* parasite infection (e.g., baseline monoterpene and VOC concentrations).

The current invention is further directed to methods of detecting select volatile organic chemicals in samples of exhaled breath or condensed breath from a subject. In some embodiments, the methods comprise detecting of at least one monoterpene in a subject by analyzing a sample of exhaled breath or condensate breath obtained from the subject for at least one monoterpene (e.g., α-pinene and/or 3-carene) as described herein. In other embodiments, the methods comprise detecting a series of volatile organic chemicals in a subject and determining a concentration for each of the VOCs. The series of VOCs can include (1)

isoprene, (2) nonanal, (3) tridecane, (4) 4-methyl undecane, (5) 3,7-dimethyl decane, and (6) 2,3,4-trimethyl hexane. In further embodiments, the methods of detecting volatile organic chemicals in a sample comprise the combination of any of the methods described herein. Specifically, various embodiment of the invention comprise detecting a monoterpene and the series of VOCs as described herein.

In still further embodiments of the present invention, the methods of analyzing breath samples for monoterpenes and/or the series of VOCs further comprises analyzing the same sample for one or more one or more volatile organic chemicals selected from the group consisting of allyl methyl sulfide, 1-methylthopropane, (E)-1-methylthio-1-propene, (Z)-1-methylthio-1-propene, and combinations thereof.

In the methods described herein, the sample obtained from the subject is exhaled breath. In some embodiments, the methods further comprise condensing or concentrating the sample before analysis.

In various embodiments of the present invention, the subject is a human. In various embodiments, the subject is a human of about 10 years of age or less, from about 11 to about 20 years of age, or greater than about 20 years of age.

In various embodiments, the subject exhibits one or more characteristic symptoms or etiology known to be associated with a *Plasmodium* parasite infection. These include, but are not limited to, high fever, prostration, impaired consciousness, respiratory distress (acidotic breathing), gastrointestinal distress, multiple convulsions, circulatory collapse, pulmonary edema, abnormal bleeding, jaundice, dizziness, confusion, disorientation, coma, headache, back pain, myalgia, chills, coughing, and/or hemoglobinuria.

The methods of the present invention can further comprise administering to the subject a pharmaceutical composition comprising a therapeutically effective amount of at least one compound effective against the *Plasmodium* parasite infection. For example, the compound effective against the *Plasmodium* infection can include at least one antimalarial drug selected from the group consisting of quinine, derivatives of quinine, semi-synthetic artemesinins, atovaquone, proguanil, pharmaceutically acceptable salts thereof, and combinations thereof. In some embodiments the compound effective against the *Plasmodium* infection comprises an artemesinin.

The invention is further directed towards compositions and methods for attracting mosquitoes for use in traps or pest-control system. In various embodiments, the mosquito attractant composition comprises a matrix and at least one attractant compound. In other embodiments, the mosquito attractant composition comprises a carrier fluid (e.g., gas, liquid, gel, etc.) and at least one attractant compound. In various embodiments, the at least one attractant compound comprises α-pinene and/or 3-carene. In some embodiments the at least one attractant compound comprises a combination of α-pinene and 3-carene. In certain embodiments, the mosquito attractant compound further comprises 1-octen-3-ol (octenol) and/or carbon dioxide. For example, attractant compounds can comprise α-pinene and/or 3-carene in any combination with 1-octen-3-ol and/or carbon dioxide.

In various embodiments, the matrix used is any substance capable of presenting the attractant compound to a mosquito. A non-limiting list of suitable matrices includes waxes, emulsion, wax emulsion, fibers, plastics, candles and combinations thereof. Additional matrices suitable for the present invention include specially formulated waxy or wax-like medium or vehicle engineered to release desired amounts of vaporous attractant compound at ambient temperatures. Alternatively, the matrix can be a porous medium suitable for releasing effective amounts of the attractant compound. For example, a suitable matrix is polyester membrane material having micropores encasing a block of attractant compound saturated fibers that gradually releases the attractant compound so that it permeates the microporous membrane and is released to the environment. In various embodiments, the matrix comprises an organic medium or a synthetic organic medium, such as those described above.

In various embodiments, the carrier fluid comprises a gas such as nitrogen, carbon dioxide, oxygen, air, or mixtures thereof (e.g., carbon dioxide enriched air).

In various embodiments, the mosquito attractant composition comprises at least about 10 wt. %, at least about 20 wt. %, at least about 30 wt. %, at least about 40 wt. %, at least about 50 wt. %, at least about 60 wt. %, at least about 70 wt. %, at least about 80 wt. %, or at least about 90 wt. % of the at least one attractant compound. In some embodiments, the mosquito attractant composition comprises from about 10 wt. % to about 95 wt. %, from about 25 wt. % to about 95 wt. %, from about 50 wt. % to about 95 wt. %, from about 10 wt. % to about 75 wt. %, from about 25 wt. % to about 75 wt. %, or from about 50 wt. % to about 75 wt. % of the at least one attractant compound. In various embodiments, the mosquito attractant composition comprises at least about 0.0001 wt. %, at least about 0.001 wt. %, at least about 0.01 wt. %, at least about 0.1 wt. %, or at least about 1 wt. % of the at least one attractant compound. In other embodiments, the mosquito attractant composition comprises from about 0.001 wt. % to about 95 wt. %, from about 0.01 wt. % to about 95 wt. %, from about 0.1 wt. % to about 95 wt. %, or from about 1 wt. % to about 95 wt. % of the at least one attractant compound.

In accordance with various embodiments of the invention, a method for attracting mosquitos comprises emitting from a trap or system an amount of at least one attractant compound selected from the group consisting of α-pinene, 3-carene, and combinations thereof. In some embodiments the method for attracting mosquitoes further comprises emitting 1-octen-3-ol (octenol) from the trap or system. In certain embodiments, the method for attracting mosquitoes further comprises emitting carbon dioxide from the trap or system.

EXAMPLES

The following non-limiting example(s) are provided to further illustrate the present invention.

Example 1

Breath Sample Collection from Two Cohorts from Malawi and Analysis with Gas Chromatography/Mass Spectrometry (GC/MS)

Breath Collection

Two independent cohorts were recruited, both from two ambulatory pediatric centers in Lilongwe, Malawi. Samples from each cohort were collected in separate two week periods during 2015-2016. Children aged 3-15 were eligible for inclusion in the study if, in the course of routine care, their clinician determined a need for malaria testing. Children were excluded if they had severe or cerebral malaria, required urgent medical intervention, had received antimalarial therapy within the past week, were known to have diabetes or chronic kidney or liver disease, or were uncooperative with breath sampling. Malaria rapid diagnostic test (MRDT) results were confirmed with malaria parasite smears; children with both positive MRDT and blood smear were classified as having malaria and those with both negative MRDT and blood smear were enrolled as controls. A summary of demographic and clinical characteristics for Cohorts 1 and 2 are depicted in Tables 1 and 2 below. Data are represented as number (%) except for age. If one or more patients were excluded, number given is fraction of total. IQR is interquartile range. Chronic and acute malnutrition were defined respectively as height-for-age Z-score or BMI-for-age Z-score two or more standard deviations below median. Fisher's exact test or Mann-Whitney U-test were used, as appropriate, to calculate p values.

TABLE 1

Baseline patient demographic and clinical characteristics for Cohort 1

|  | Malaria Positive (n = 17) | Malaria Negative (n = 18) | p value |
|---|---|---|---|
| Demographics |  |  |  |
| Age, median years (IQR) | 8 (6-10) | 7 (5-8.5) | 0.33 |
| Female, n (%) | 8 (47) | 10/17 (59) | 0.73 |
| Reported Symptoms, n (%) |  |  |  |
| Fever | 16 (94) | 15 (83) | 0.60 |
| Diarrhea | 0 (0) | 2 (11) | 0.49 |
| Vomiting | 5 (29) | 4 (22) | 0.71 |
| Headache | 16 (94) | 14 (78) | 0.34 |
| Abdominal Pain | 13 (76) | 17 (94) | 0.18 |
| Muscle/Joint Pain | 12 (71) | 4 (22) | 0.007 |
| Other, n (%) |  |  |  |
| Chronic Malnutrition | 5/16 (31) | 3 (17) | 0.43 |
| Acute Malnutrition | 0/16 (0) | 1 (6) | 1 |
| Use Bed Net | 9 (53) | 10 (56) | 1 |
| Malaria within past 3 months | 3 (18) | 5/17 (29) | 0.69 |

TABLE 2

Baseline patient demographic and clinical characteristics for Cohort 2

|  | Malaria Positive (n = 26) | Malaria Negative (n = 21) | p value |
|---|---|---|---|
| Demographics |  |  |  |
| Age, median years (IQR) | 9 (7-10) | 6 (4-8.5) | 0.02 |
| Female, n (%) | 15 (58) | 5 (24) | 0.04 |
| Reported Symptoms, n (%) |  |  |  |
| Fever | 25 (96) | 18 (86) | 0.31 |
| Diarrhea | 3 (12) | 3 (14) | 1 |
| Vomiting | 13 (50) | 6 (29) | 0.23 |
| Headache | 21 (81) | 14 (67) | 0.33 |
| Abdominal Pain | 16 (62) | 14 (67) | 0.77 |
| Muscle/Joint Pain | 16 (62) | 7 (33) | 0.08 |
| Other, n (%) |  |  |  |
| Chronic Malnutrition | 7 (27) | 2/20 (10) | 0.26 |
| Acute Malnutrition | 1 (4) | 2/20 (10) | 0.57 |
| Use Bed Net | 11 (42) | 18 (86) | 0.003 |
| Malaria within past 3 months | 6/24 (25) | 3 (14) | 0.47 |

After informed consent was obtained from caretakers, vital signs and anthropometry were taken and a brief demographic and health history form was completed. Blood for thick and thin smears was drawn and stored in a cooler with ice packs.

Breath samples were obtained using two methods. For Cohort 1, alveolar breath collection was performed as previously reported with alterations detailed here (Berna et al., J. Infect. Dis. 212, 1120-1128 (2015). At least 1 L of breath was collected from each participant in a 3 L SamplePro Flexfilm sample bag (SKC Inc.). Participants exhaled into the bag using a custom made adapter fitted with a replaceable cardboard mouthpiece. Exactly 1 L of collected breath was pumped from the collection bag through an inert stainless steel sorbent tube (Tenax 60/80/Carbograph 1 60/80/Carboxen 1003 40/60, Camsco), a small metal tube packed with resin which absorbs non-polar molecules, for transportation and analysis. A set flow pump (ACTI-VOC, Markes International) calibrated to 100 mL/min was used to transfer sample breath from the collection bag through the sorbent tube.

For Cohort 2, samples were collected using a BioVOC breath sampler (Markes International), a device which collects ~100 mL of exhaled, alveolar breath (Kwak et al., Metabolites. 4, 879-888 (2014)). Study participants were instructed to take a normal breath in and then to exhale fully into the breath sampler. The collected breath sample was then flushed into a sorbent tube for transportation and analysis. Three breath samples from each participant were collected and stored on a single sorbent tube. Prior to sampling, sorbent tubes had been conditioned by flushing with 120 mL/min He at 290° C. for one hour, or with 100 mL/min He at 320° C. for two hours. Samples of room air were collected using both methods to assess possible environmental contaminants. All breath samples were stored at −20° C. prior to analysis.

Following breath sample collection, study participants returned to usual care per the recommendations of the treating clinician. Antimalarial medications were provided for participants with positive MRDT results. Demographic and anthropometric data was entered into a database and height-for-age and BMI-for-age Z-scores were calculated using Anthro Plus software (World Health Organization).

GC Mass Spectrometry Analysis:

Samples were transported from the study site to analysis location, and were analyzed by thermal desorption followed by gas chromatography/mass spectrometry (TD-GC/MS) one month after initial collection. The specific parameters followed are described below.

All samples were run with a TurboMatrix 650 ATD (Perkin Elmer) connected to a Leco Pegasus 4D GCxGC-TOFMS system. Before analysis, sorbent tubes were brought to room temperature and purged for 5 min with BiP N2 (Airgas) at 60 mL/min. A gaseous standard mixture (20.1 ng fluorobenzene, 18.6 ng toluene-D8, 21.7 ng bromofluorobenzene, 20.3 ng 1,2-dichlorobenzene-D4) was added to each tube by the TurboMatrix 650 immediately prior to analysis. Tubes were desorbed at 270° C., 40 mL/min helium flow, with recollection on a secondary Tenax cold trap at 10° C. Analytes were released from the secondary trap by heating to 295° C. with 20% transferred to the GC/MS. The GC had a 30 m length×0.25 mm ID×0.25 μm film thickness DB-5 column (Agilent). The GC oven was programmed to hold at 40° C. for 3 min, ramp 5° C./min to 200° C., then ramp 10° C./min to 250° C., final ramp 25° C./min to 300° C., then hold at 300° C. for 3 min. The TOFMS had a sampling frequency of 50 Hz and a mass recording range of 34-400 amu.

Pure reference standards of isoprene, α-pinene, and 3-carene (acquired from Sigma-Aldrich) and nonanal and tridecane (obtained from Supelco) were prepared by adding 3 μL of 10 ng/μL solution of pure standard in methanol to a sorbent tube and then immediately purging with 85 mL/min N2 for 10 min. Tubes were stored and shipped at −20° C. and run as per the GC/MS method stated above, except that flows were adjusted so 4.2% of the desorbed sample went onto the column.

Example 2

Identification and Quantification of α-Pinene and 3-Carene in Cohorts from Malawi GC/MS Data Processing GC/MS data files from Example 1 were exported in the ".cdf" format, and imported into OpenChrom (P. Wenig et al., BMC Bioinformatics. 11, 405 (2010)). The "ion remover filter" function was used to remove all ions except the m/z of interest. Then, the peak at the proper retention time (determined by comparison to a true standard) was isolated by the "first derivative peak detector" function, with threshold set to "medium," the "selected" box unticked, minimum S/N set to 0, and "moving average window size" set to 3. Finally, the base ion peak area was calculated with the "peak integrator trapezoid" function on default settings (no selected ions, no minimums, peak background not included) and normalized to the base ion peak area of 1,2-dichlorobenzene-D4. Peaks with a normalized area of 0.0002 or less were considered at/below the limit of detection.

The chemical structures of the compounds analyzed in this Example and their identifying molecular characteristics are described in Table 3 below.

TABLE 3

| Compound Name (MW) | Structure | Base Ion (m/z) | Retention Time (min) |
|---|---|---|---|
| Isoprene (68.1 g/mol) | 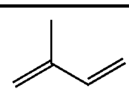 | 67 | 1.49 |
| Acetone (58.1 g/mol) | 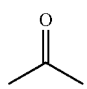 | 43 | 1.46 |
| α-pinene (136.2 g/mol) | 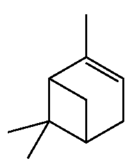 | 93 | 8.53 |
| 3-carene (136.2 g/mol) | 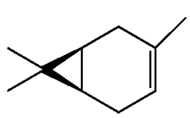 | 93 | 11.06 |

Figure 1A:
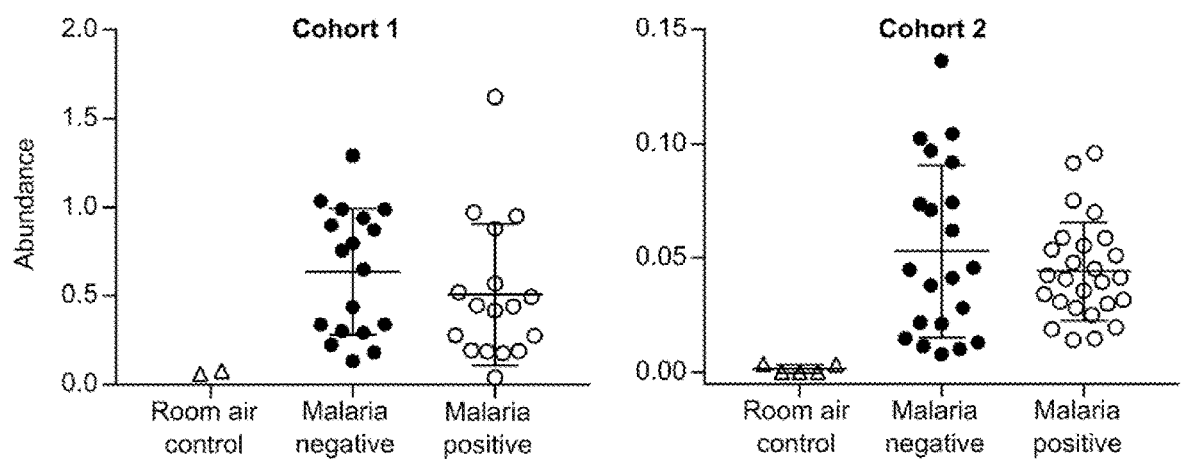
FIG. 1A shows two scatterplots of the abundance of isoprene in breath samples from two Malawian cohorts compared to ambient room air. Isoprene abundances were calculated by normalization to an internal standard.
Figure 1B:
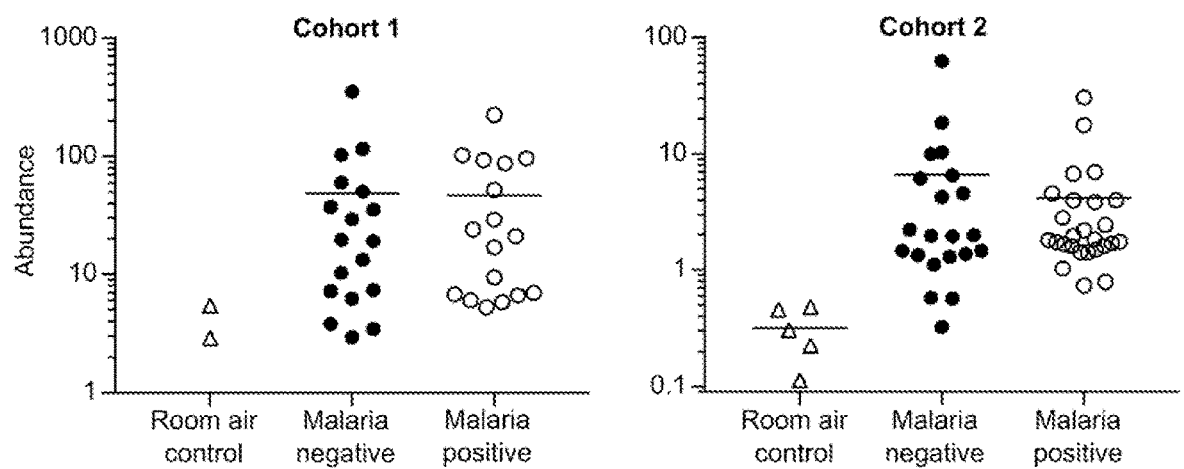
FIG. 1B shows two scatterplots of the abundance of acetone in breath samples from two Malawian cohorts compared to ambient room air. Acetone abundances were calculated by normalization to an internal standard.

To confirm that breath had been successfully collected the level of two of the most abundant/common breath metabolites, isoprene and acetone (Mochalski et al., Analyst. 138, 2134-45 (2013)), were analyzed in patient samples. One or both metabolites were found to be elevated at least two-fold compared to room air levels in each sample and levels of the two metabolites were indistinguishable between patient samples (FIGS. 1A and 1B).

Figure 2A:
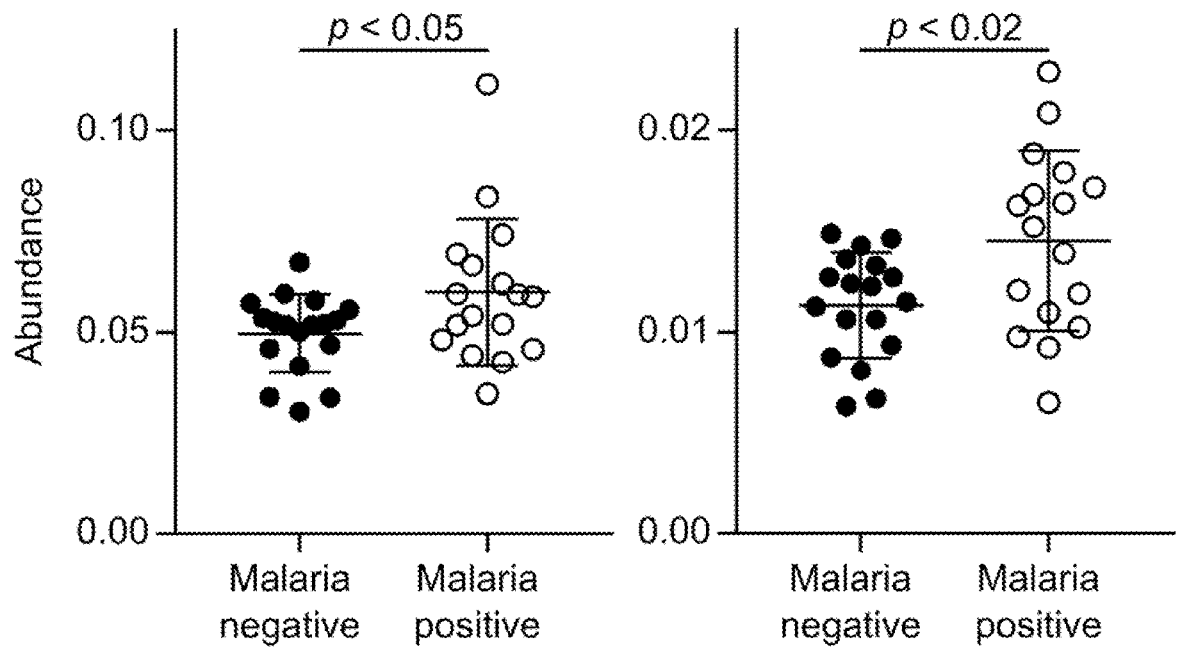
FIG. 2A is a scatterplot of the abundance of α-pinene (left plot) and 3-carene (right plot) normalized to an internal standard in a malaria positive and negative patient population (Cohort 1).
Figure 2B:
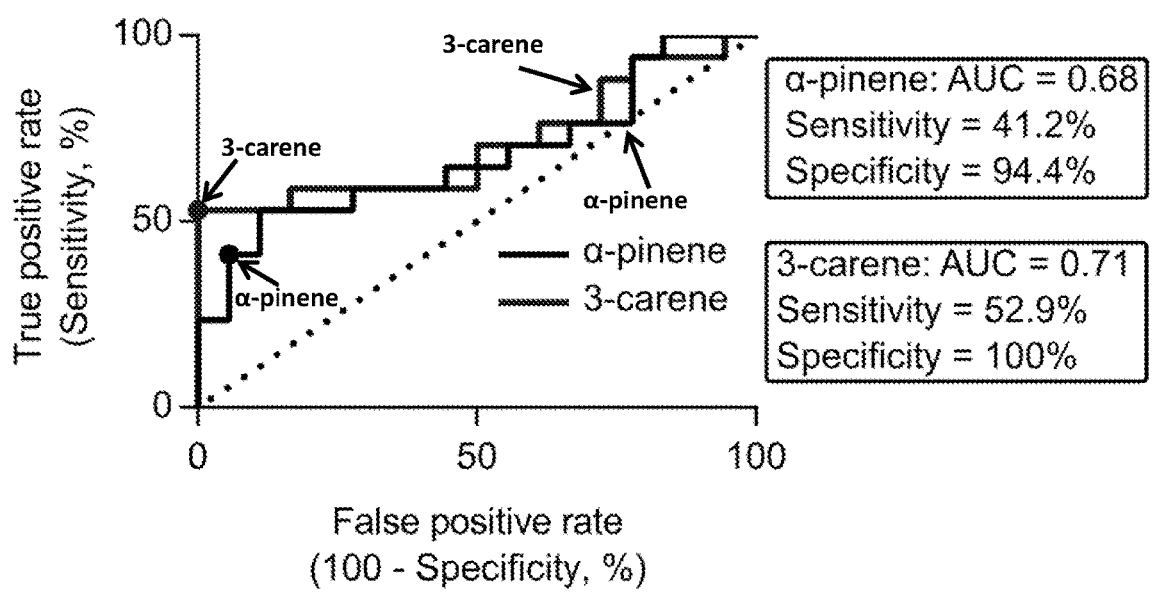
FIG. 2B is a receiver operator characteristic (ROC) curve for α-pinene (black) and 3-carene (blue) generated from the data in FIG. 2A. Boxes on right detail sensitivity and specificity of these biomarkers as determined by the position with the maximum likelihood ratio for each curve. AUC is "area under curve" and is a measure of overall accuracy.
Figure 2C:
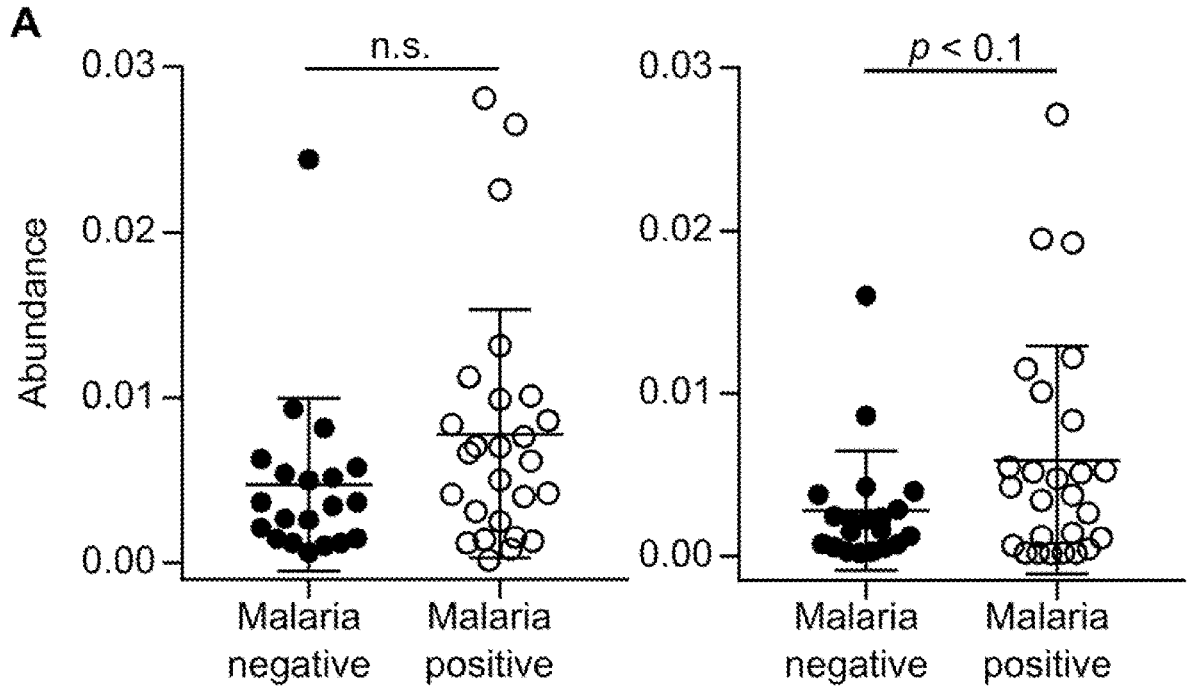
FIG. 2C is a scatterplot of the abundance of α-pinene (left plot) and 3-carene (right plot) analyzed as in FIG. 2A but from a different patient population (Cohort 2).
Figure 2D:
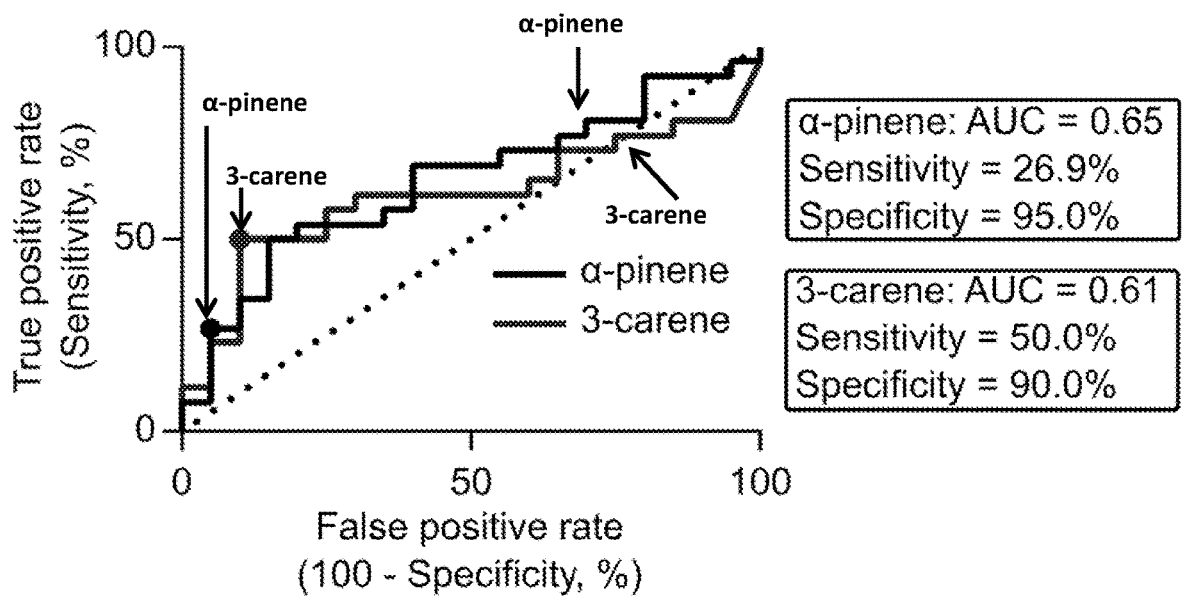
FIG. 2D is a receiver operator characteristic (ROC) curve for α-pinene and 3-carene generated from data in FIG. 2C with specificity, sensitivity and AUC for each compound indicated to the right.

Samples were then analyzed for two monoterpenes, α-pinene and 3-carene. Abundance of α-pinene and 3-carene were significantly elevated in malaria positive children of Cohort 1 (FIG. 2A) and levels of 3-carene was significantly elevated in malaria positive children of Cohort 2 (FIG. 2C). Normalized abundance values (compared to internal standards) for each patient sample were used to generate receiver operator characteristic curves (ROC) for both α-pinene and 2-carene (FIGS. 2B and 2D). The area under the curve (AUC) for each compound (0.68 [Cohort 1] and 0.65 [Cohort 2] for α-pinene; 0.71 [Cohort 1] and 0.61 [Cohort 2] for 3-carene) is a measurement of overall accuracy. Analysis of the points on the curve that had the maximum likelihood ratio show that detection of α-pinene or 3-carene correctly diagnosed patients in Cohort 1 with high specificity (α-pinene: 94.4%, 3-carene: 100%) and moderate sensitivity (41.2% and 52.9%, respectively) (FIG. 2B). In Cohort 2 they also had high specificity (95% and 90% respectively) but reduced sensitivity (26.9% and 50% respectively) (FIG. 2D). Thus, this example demonstrates that detection of α-pinene and 3-carene in breath samples can effectively diagnose malaria with high specificity and moderate sensitivity.

Example 3

Cumulative VOC Abundance Accurately Diagnoses Malarial Infection

Initial Data Processing and Abundance Visualization

The overall VOC profile of patient samples in Example 1 was acquired in the following manner. The ".cdf" GC/MS data files were converted to ".D" via GC/MS Translator Pro (ChemSW, Inc.), and then modified to work with MassHunter via GC/MS ChemStation File Translation software (Agilent). Files were deconvoluted using the "Find Compounds by Chromatogram Deconvolution" feature in MassHunter Qualitative Analysis (Agilent). RT window size factor was set to 75. Delta m/z was −0.3 amu/+0.7 amu. There was no peak sharpness, spectrum peak, or SNR threshold set. Absolute mass height threshold was set to ≥500 counts, and absolute area was set to ≥1000 counts; no relative threshold was set for either mass height or absolute area. Deconvoluted compound lists were imported into Mass Profiler Professional (Agilent) for alignment. Compounds were required to have ≥2 ions. Alignment parameters were Tolerance=0.1, Match Factor=0.2, deltaMZ=0.2. Peaks were normalized to the 1,2-dichlorobenzene-D4 internal standard (m/z 150@11.7 min). Compounds were given annotations using the "IDBrowser Identification" feature using the NIST v11 reference library. M/z expansion was set to −0.3 amu/+0.7 amu. RT matching was not employed. Minimum match score was set to 40. Compounds present in only one sample were filtered out, as were siloxane contaminants.

To visualize the relative abundance of each VOC in a patient sample, standardized GC/MS spectra (following removal of contaminants and normalization) underwent logarithmic compression by applying a $\log_2$ operator to compress the abundance values obtained from each subject. In FIGS. 4A and 4B, logarithmically compressed VOC abundances are presented on a rainbow scale where blue represents low abundance and red represents high abundance.

Classifier

An aligned, standardized compound list generated by Mass Profiler Professional was exported and internal standards and silicone/siloxane contaminants were manually removed. Only VOCs that were present in at least 20 participants were used in analysis, leaving 42 potential biomarkers. Class labels were assigned to each subject based on their diagnosis, as follows: 1 for malaria negative and 2 for malaria positive.

First, VOCs were sorted based on their correlation with class labels of whether malaria was diagnosed. Higher correlation magnitudes indicated greater suitability as a biomarker for malaria. To classify a subject, the abundances of the six most correlated VOCs were summed in order of correlation magnitude. The abundances of negatively correlated VOCs were subtracted from the overall cumulative value. A nearest mean classification algorithm (binary classification) with leave-one-breath-sample-out cross validation scheme was followed. In this approach, mean cumulative VOC abundances for both classes were computed and used to generate a classification model. All samples were included in generating the model. Each breath sample was then systematically classified based on the class mean to which it was closest. The classification scheme was validated by repeating the same algorithm, but using a model generated from all samples except the one to be classified ("leave-one-out cross validation"). The predicted label [malaria (+) or malaria (−)], was compared with the actual values in order to quantify the performance of the method.

Figure 3A:
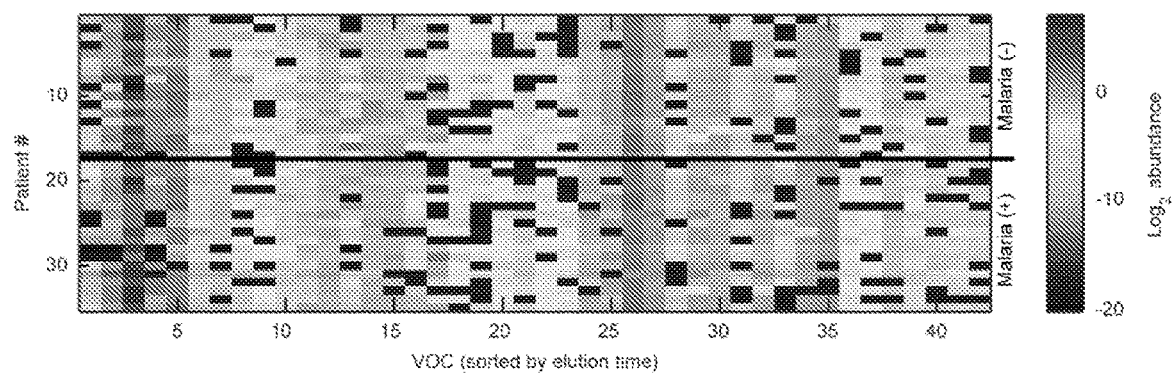
FIG. 3A is a heat map of the $\log_2$(abundance) of 43 volatile organic chemicals (VOCs) sorted as columns by elution time. Rows represent individual patients. The black horizontal line separates *Plasmodium* positive from *Plasmodium* negative patients.
Figure 3B:
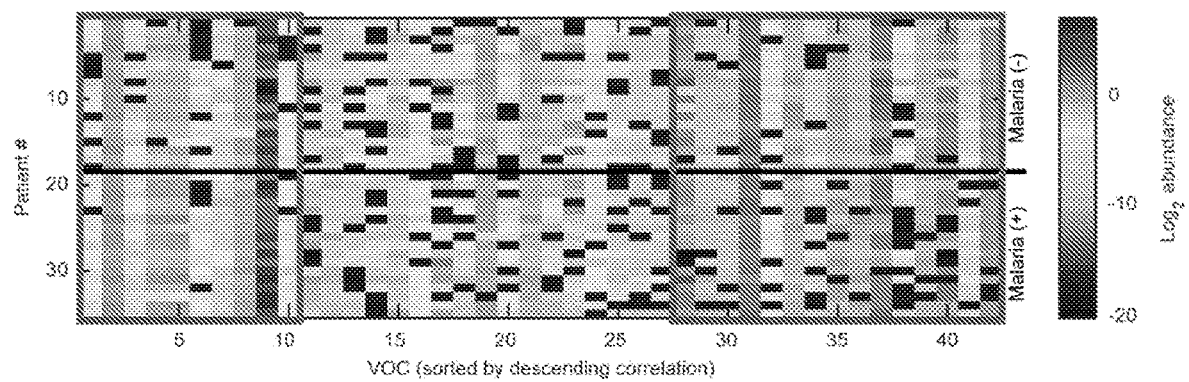
FIG. 3B is a heat map of the same data in FIG. 3A but with VOCs sorted by descending correlation to *Plasmodium* status.
Figure 3C:
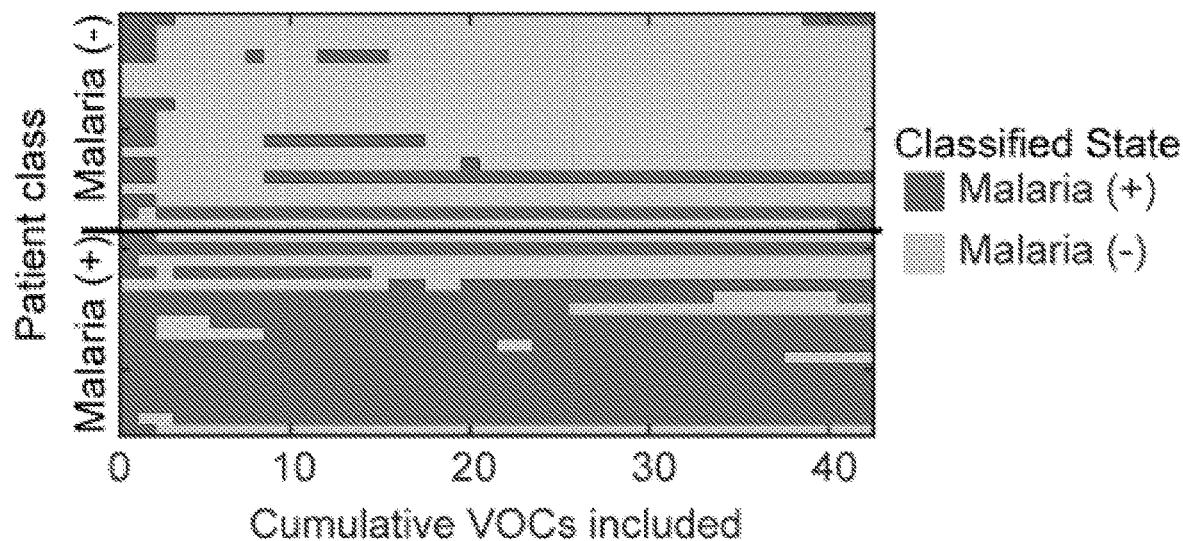
FIG. 3C is a plot of patient classification as either malaria positive (red) or negative (blue). Each row represents a patient sorted by actual malaria status. Each column represents a new set of classifications generated by including increasing numbers of VOCs in the analysis (y axis).
Figure 3D:
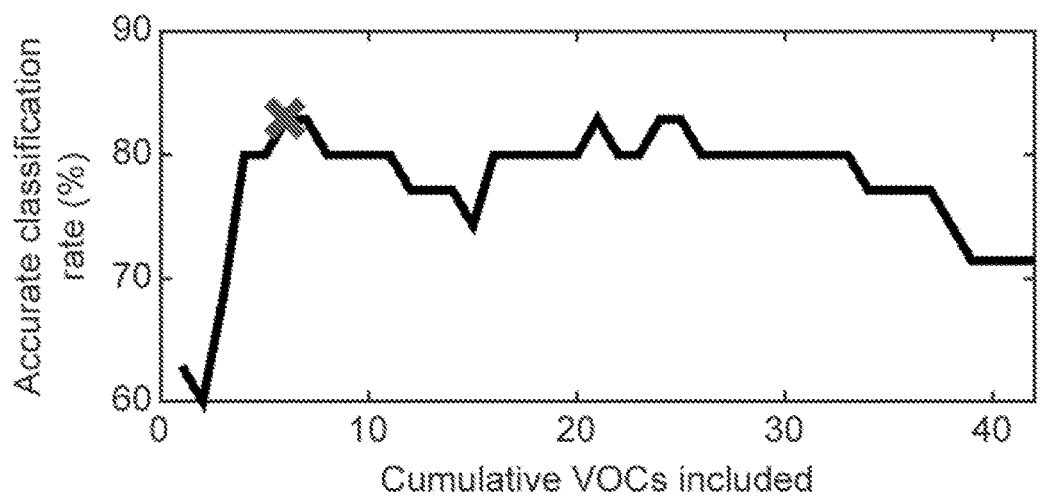
FIG. 3D is a line plot of accurate classification rate (%) versus the cumulative number of VOCs included in the analysis. The red X indicates peak accuracy and corresponds to 6 VOCs.

FIGS. 3A and 3B depict combined heat maps of all patient VOC profiles (generated using methods described above). In each graph, each row represents a patient (sorted by malaria diagnosis) and each column represents one of the 42 potential biomarkers identified. This data is presented in tabular form below. In FIG. 3A the VOCs are sorted by elution time and no correlation with malaria diagnosis is apparent. In FIG. 3B, the VOCs are sorted by descending correlation following the method described above. The red boxes highlight regions of expression difference between the two subject groups. Compounds furthest to the left correlate most strongly with positive patients while the compounds furthest to the right correlate most strongly with negative patients. The middle compounds do not vary significantly with infection. FIG. 3C depicts a classification map of all patients generated by cumulative abundances of increasing numbers of VOCs. The top half depicts malaria negative patients, the bottom half shows malaria positive subjects. The classified states are red for malaria (+) and blue for malaria (−). It is evident that accuracy of classification peaks after inclusion of a few VOCs. FIG. 3D depicts the diagnostic accuracy as a function of the number of VOCs included and confirms that it peaks at 83% using as few as six VOCs. Leave-one-out cross validation, described earlier, yielded an accurate classification rate of 77%. Based on this metric, six VOCs were further examined for use as a diagnostic footprint.

| Compound Annotation | Malaria Negative | | | | | | | | |
| --- | --- | --- | --- | --- | --- | --- | --- | --- | --- |
| | Patient 1 | Patient 2 | Patient 3 | Patient 4 | Patient 5 | Patient 6 | Patient 7 | Patient 8 | Patient 9 |
| Formamide | −2.09 | −19.73 | −3.20 | −19.33 | −1.09 | −3.42 | −2.94 | −1.45 | −19.76 |
| Isopropyl Alcohol | −0.20 | −1.57 | −0.34 | −0.53 | −1.22 | −1.76 | 0.04 | 1.76 | −3.42 |
| Acetone | 2.66 | 2.51 | 5.02 | 1.12 | 3.18 | 1.57 | 0.00 | 6.03 | −19.76 |
| Cyclopropane, ethylidene- | −1.85 | 0.07 | 0.00 | −1.64 | −1.17 | −2.65 | 0.01 | −3.50 | 0.04 |
| 2-Propanol, 1,3-dichloro- | 1.37 | 0.09 | 0.41 | 0.48 | 0.69 | −1.86 | −0.23 | 0.98 | 0.10 |
| 1,3-Hexadien-5-yne | −3.26 | −2.86 | −2.81 | −2.98 | −3.13 | −3.16 | −3.98 | −3.09 | −3.23 |
| O-Butylisourea | −19.04 | −2.52 | −2.66 | −2.91 | −19.15 | −2.02 | −1.80 | −2.19 | −2.89 |
| 2-Butanone, 3-methyl- | −19.04 | −3.51 | −2.32 | 4.58 | 4.02 | −4.32 | −5.11 | −1.59 | −3.21 |
| Hydroxylamine, O-(2-methylpropyl)- | −4.61 | −19.73 | −4.17 | −4.70 | −2.65 | −3.88 | −5.17 | −4.66 | −5.44 |
| Methyl methacrylate | −3.37 | −3.89 | −3.30 | −3.45 | −3.85 | 19.80 | −3.77 | −4.63 | −3.23 |
| 1,3,5-Cycloheptatriene | −3.32 | −2.36 | −1.67 | −3.38 | −3.60 | −3.99 | −3.35 | −2.28 | −3.59 |
| 4-Ethylbenzamide | −2.16 | −2.51 | −1.33 | −1.03 | −2.28 | −2.82 | −2.16 | −1.85 | −2.27 |
| Hexanal | −19.04 | −19.73 | −3.23 | −1.46 | 19.15 | −3.52 | −3.94 | −2.36 | −4.42 |
| Hexane, 2,3,4-trimethyl- | −1.81 | −2.20 | −2.13 | −2.40 | −2.21 | −2.67 | −1.95 | −1.62 | −2.63 |
| Methoxyacetic acid, hexyl ester | −1.90 | −2.49 | −2.36 | −2.64 | −2.17 | −2.75 | −2.06 | −1.99 | −2.13 |
| p-Xylene + 6.4320683 | −3.65 | −2.23 | −3.32 | −3.24 | −19.15 | −3.31 | −3.14 | −2.29 | −6.04 |
| 1,3-Cyclopentadiene, 5-(1-methylethylidene)- | −3.77 | −19.73 | −1.92 | −19.33 | −4.17 | −5.86 | −5.02 | −0.12 | −19.76 |
| Acetic acid, 2-phenylethyl ester + 7.1055326 | −4.38 | −4.44 | −4.31 | −4.22 | −5.04 | −5.28 | −4.55 | −5.70 | −5.70 |
| Cyclohexanone | −19.04 | −3.96 | −4.41 | −4.49 | −3.53 | −5.24 | −4.75 | −2.07 | −4.47 |
| Bicyclo[3.1.0]hex-2-ene, 4-methyl-1-(1-methylethyl)- | −4.67 | −4.87 | −19.40 | −19.33 | −19.15 | −5.23 | −4.78 | −4.52 | −4.33 |
| Pentane, 2,2,3-trimethyl- | −3.63 | −4.34 | −3.47 | −2.55 | −19.15 | 4.29 | −3.91 | −19.43 | −19.76 |
| Pentane, 2,2,3,4-tetramethyl- + 9.821276 | −4.84 | −6.26 | −19.40 | −4.56 | −5.10 | −5.36 | −5.11 | −19.43 | −5.01 |
| Hexane, 1-chloro- | −19.04 | −19.73 | −19.40 | −19.33 | −19.15 | −6.36 | −4.95 | −3.44 | −5.01 |
| Heptane, 2,2,4,6,6-pentamethyl- | −2.51 | −2.86 | −2.32 | −1.71 | −2.76 | −2.85 | −2.75 | −2.30 | −2.61 |
| Cyclohexene, 1-methyl-4-(1-methylethenyl)-, (S)- | −1.66 | −1.37 | −2.09 | −19.33 | −1.45 | −1.93 | −1.91 | −1.85 | −1.84 |
| 1-Hexanol, 2-ethyl- | 1.12 | 0.73 | 0.61 | 0.65 | 1.16 | 0.14 | 0.30 | 1.29 | 0.64 |
| 1-Nonene, 4,6,8-trimethyl- | −1.16 | −1.59 | −1.09 | −0.59 | −1.33 | −1.76 | −1.40 | −0.89 | −1.37 |
| Decane, 2,5,9-trimethyl- | −3.78 | −4.17 | −3.57 | −2.94 | −19.15 | −3.93 | −4.01 | −3.30 | −19.76 |
| Pentane, 2,2,3,4-tetramethyl- | −2.10 | −2.44 | −1.92 | −1.20 | −2.27 | −2.96 | −2.29 | −1.79 | −2.20 |
| Hexane, 2,3,4-trimethyl- + 12.597675 | −19.04 | −2.15 | −1.87 | −1.61 | −1.74 | −2.27 | −1.79 | −1.56 | −1.79 |
| Oxalic acid, allyl nonyl ester | −3.51 | −3.80 | −3.53 | −19.33 | −19.15 | −19.80 | −3.41 | −3.30 | −3.41 |
| Hexane, 2,2,3-trimethyl- | −19.04 | −2.49 | −2.07 | −1.38 | −2.70 | −5.12 | −2.59 | −1.79 | −2.51 |
| Pentane, 2,2,3,4-tetramethyl- + 13.338136 | −3.78 | −19.73 | −19.40 | −2.59 | −19.15 | −4.28 | −3.93 | −19.43 | −3.76 |
| Octane, 3,5-dimethyl- | −19.04 | −1.79 | −1.74 | −1.41 | −1.52 | −2.15 | −1.60 | −1.25 | −1.58 |
| 2-Nonen-1-ol, (E)- | −2.53 | −0.76 | −1.00 | −0.78 | −1.00 | −1.36 | −1.23 | −0.46 | −1.06 |
| Hexane, 3-methyl- | −4.36 | −4.37 | −4.64 | −3.60 | −19.15 | −19.80 | −20.00 | −3.45 | −4.07 |
| Propanoic acid, 2-hydroxy-, pentyl ester | −5.23 | −4.66 | −19.40 | −3.66 | −4.20 | −5.99 | −4.21 | −5.14 | −4.90 |

-continued

| Compound Annotation | | | | | | | | | |
|---|---|---|---|---|---|---|---|---|---|
| Octane, 3,5-dimethyl- + 17.273 | −2.68 | −2.25 | −2.64 | −2.93 | −2.86 | −19.80 | −2.95 | −1.72 | −2.62 |
| 2,3-Epoxyhexanol | −4.16 | −4.03 | −4.01 | −3.34 | −19.15 | −3.47 | −4.14 | −19.43 | −4.02 |
| Hexane, 2,3,4-trimethyl- + 19.489073 | −3.18 | −19.73 | −3.19 | −2.97 | −3.25 | −3.87 | −3.26 | −3.05 | −3.15 |
| Hexane, 2,4-dimethyl- | −3.58 | −3.30 | −3.58 | −3.92 | −3.56 | −3.91 | −3.87 | −2.69 | −3.55 |
| Hexane, 2,3,4-trimethyl- + 20.846872 | −19.04 | −3.86 | −3.25 | −3.01 | −3.55 | −3.90 | −20.00 | −19.43 | −3.48 |

| | Malaria Negative | | | | | | | | |
|---|---|---|---|---|---|---|---|---|---|
| Compound Annotation | Patient 10 | Patient 11 | Patient 12 | Patient 13 | Patient 14 | Patient 15 | Patient 16 | Patient 17 | Patient 18 |
| Formamide | −3.26 | −19.61 | −3.20 | −20.61 | −3.19 | −3.40 | −3.20 | −20.66 | −3.45 |
| Isopropyl Alcohol | 0.21 | −3.54 | −0.03 | −3.17 | −0.70 | 0.36 | −1.49 | −20.66 | −1.68 |
| Acetone | 3.86 | 0.26 | 3.41 | 0.05 | 4.15 | 1.63 | 3.50 | 1.47 | 1.93 |
| Cyclopropane, ethylidene- | 0.37 | −1.35 | 0.11 | −0.17 | −0.46 | −0.02 | 0.55 | −20.66 | −1.04 |
| 2-Propanol, 1,3-dichloro- | 1.00 | 0.51 | 0.91 | −1.16 | −1.13 | 1.05 | 0.74 | −2.02 | 0.20 |
| 1,3-Hexadien-5-yne | −2.30 | −3.98 | −3.43 | −3.44 | −2.42 | −4.04 | −2.39 | −2.31 | −3.69 |
| O-Butylisourea | −2.62 | −2.84 | −2.47 | −2.61 | −2.91 | −3.12 | −2.44 | −5.20 | −2.77 |
| 2-Butanone, 3-methyl- | −3.11 | −4.83 | −3.56 | −4.87 | −3.15 | −4.91 | −19.34 | −20.66 | −19.68 |
| Hydroxylamine, O-(2-methylpropyl)- | −3.57 | −19.61 | −19.33 | −3.85 | −3.49 | −5.54 | −4.01 | −20.66 | −19.68 |
| Methyl methacrylate | −2.63 | −4.62 | −3.32 | −4.13 | −5.31 | −3.19 | −3.37 | −3.84 | −3.52 |
| 1,3,5-Cycloheptatriene | −2.03 | −2.87 | −3.29 | −2.03 | −1.96 | −3.77 | −3.52 | −3.97 | −3.98 |
| 4-Ethylbenzamide | −2.11 | −2.34 | −1.30 | −2.67 | −1.92 | −2.81 | −1.78 | −2.68 | −2.19 |
| Hexanal | −1.64 | −3.59 | −3.36 | −1.19 | −1.87 | 4.25 | 0.11 | −3.89 | −2.43 |
| Hexane, 2,3,4-trimethyl- | −2.28 | −0.40 | −0.85 | −1.58 | −2.97 | −2.21 | −1.38 | −2.63 | −1.27 |
| Methoxyacetic acid, hexyl ester | −2.25 | −2.18 | −1.29 | −2.29 | −3.38 | −1.65 | −1.62 | −0.54 | −1.60 |
| p-Xylene + 6.4320683 | −19.13 | −2.10 | −2.70 | −2.97 | −2.35 | −2.46 | −4.74 | −20.66 | −2.35 |
| 1,3-Cyclopentadiene, 5-(1-methylethylidene)- | −1.49 | −4.00 | −19.33 | −20.61 | −2.31 | −0.78 | −5.27 | −3.26 | −19.68 |
| Acetic acid, 2-phenylethyl ester + 7.1055326 | −4.86 | −4.11 | −19.33 | −3.55 | −19.88 | −4.50 | −4.13 | −4.67 | −5.25 |
| Cyclohexanone | −2.97 | −19.61 | −19.33 | −4.84 | −19.88 | −3.09 | −4.59 | −5.29 | −19.68 |
| Bicyclo[3.1.0]hex-2-ene, 4-methyl-1-(1-methylethyl)- | −4.63 | −19.61 | −4.20 | −5.03 | −4.84 | −4.69 | −4.39 | −5.11 | −4.53 |
| Pentane, 2,2,3-trimethyl- | −3.48 | −3.17 | −3.30 | −4.09 | −4.60 | −3.65 | −3.15 | −4.36 | −19.68 |
| Pentane, 2,2,3,4-tetramethyl- + 9.821276 | −4.69 | −19.61 | −4.46 | −5.24 | −5.45 | −4.77 | −4.43 | −5.09 | −5.36 |
| Hexane, 1-chloro- | −4.12 | −3.24 | −19.33 | −4.35 | −6.09 | −4.58 | −19.34 | −4.94 | −6.24 |
| Heptane, 2,2,4,6,6-pentamethyl- | −2.30 | −2.48 | −2.12 | −3.12 | −2.99 | −2.41 | −1.81 | −3.11 | −1.86 |
| Cyclohexene, 1-methyl-4-(1-methylethenyl)-, (S)- | −1.57 | −1.56 | −1.58 | −1.40 | −2.25 | −1.65 | −1.68 | −2.68 | −1.53 |
| 1-Hexanol, 2-ethyl- | 1.16 | 0.74 | 0.83 | −0.56 | 0.14 | 1.33 | 0.99 | −0.22 | 0.94 |
| 1-Nonene, 4,6,8-trimethyl- | −1.01 | −1.40 | −0.90 | −2.23 | −1.91 | −1.24 | −0.75 | −1.99 | −0.84 |
| Decane, 2,5,9-trimethyl- | −3.55 | −19.61 | −3.74 | −20.61 | −4.08 | −3.45 | −3.53 | −4.52 | −19.68 |
| Pentane, 2,2,3,4-tetramethyl- | −1.86 | −2.19 | −1.69 | −2.87 | −2.51 | −4.73 | −1.55 | −2.83 | −1.57 |
| Hexane, 2,3,4-trimethyl- + 12.597675 | −1.85 | −1.88 | −1.22 | −2.69 | −4.97 | −1.39 | −1.28 | −2.66 | −1.23 |
| Oxalic acid, allyl nonyl ester | −3.50 | −3.50 | −2.99 | −20.61 | −4.13 | −2.78 | −2.94 | −4.25 | −2.80 |
| Hexane, 2,2,3-trimethyl- | −2.29 | −2.18 | −1.98 | −3.13 | −2.56 | −19.03 | −1.98 | −3.40 | −1.81 |
| Pentane, 2,2,3,4-tetramethyl- + 13.338136 | −4.24 | −3.72 | −3.27 | −20.61 | −19.88 | −3.52 | −19.34 | −4.58 | −5.53 |
| Octane, 3,5-dimethyl- | −1.68 | −1.72 | −1.15 | −2.59 | −2.17 | −1.19 | −1.27 | −2.55 | −1.15 |
| 2-Nonen-1-ol, (E)- | −0.75 | −0.63 | −0.74 | −1.40 | −0.70 | −0.85 | −0.75 | −1.58 | −0.51 |
| Hexane, 3-methyl- | −4.52 | −4.49 | −19.33 | −5.25 | −4.76 | −19.03 | −4.07 | −6.69 | −19.68 |
| Propanoic acid, 2-hydroxy-, pentyl ester | −4.13 | −4.69 | −5.89 | −4.32 | −19.88 | −5.47 | −4.61 | −20.66 | −3.67 |
| Octane, 3,5-dimethyl- + 17.273 | −2.71 | −1.96 | −2.57 | −3.42 | −2.08 | −2.68 | −19.34 | −3.88 | −2.74 |
| 2,3-Epoxyhexanol | −19.13 | −2.59 | −3.44 | −4.33 | −3.83 | −3.13 | −4.56 | −4.59 | −3.52 |
| Hexane, 2,3,4-trimethyl- + 19.489073 | −3.51 | −3.47 | −2.74 | −20.61 | −4.00 | −3.09 | −2.68 | −3.67 | −19.68 |
| Hexane, 2,4-dimethyl- | −3.77 | −2.92 | −3.41 | −4.19 | −3.35 | −3.52 | −3.61 | −4.31 | −3.41 |
| Hexane, 2,3,4-trimethyl- + 20.846872 | −3.67 | −3.67 | −3.00 | −3.71 | −19.88 | −19.03 | −2.98 | −3.75 | −2.82 |

| | Malaria Positive | | | | | | | | |
|---|---|---|---|---|---|---|---|---|---|
| Compound Annotation | Patient 19 | Patient 20 | Patient 21 | Patient 22 | Patient 23 | Patient 24 | Patient 25 | Patient 26 | Patient 27 |
| Formamide | −4.30 | −3.47 | −2.21 | −2.62 | −1.51 | −20.20 | −20.23 | −2.27 | −0.87 |
| Isopropyl Alcohol | −1.70 | −0.44 | −0.31 | −0.53 | −2.01 | −1.05 | −2.41 | −1.71 | −1.43 |
| Acetone | 1.02 | 5.00 | 3.14 | 0.85 | 1.29 | 1.06 | 1.32 | 2.74 | 1.07 |
| Cyclopropane, ethylidene- | −0.14 | −2.38 | −0.68 | −0.74 | −0.97 | −20.20 | −20.23 | −0.90 | −2.24 |

-continued

| Compound Annotation | | | | | | | | | |
|---|---|---|---|---|---|---|---|---|---|
| 2-Propanol, 1,3-dichloro- | -0.55 | 0.65 | 0.57 | 0.48 | 1.21 | -1.44 | -1.69 | 0.21 | 0.09 |
| 1,3-Hexadien-5-yne | -3.30 | -2.22 | -3.46 | -2.96 | -3.35 | -3.27 | -4.07 | -1.87 | -3.69 |
| O-Butylisourea | -3.03 | -2.69 | -2.92 | -2.55 | -2.44 | -2.13 | -2.74 | -2.86 | -2.76 |
| 2-Butanone, 3-methyl- | -4.53 | -3.29 | -19.56 | -4.14 | -4.28 | -20.20 | -3.42 | -19.42 | -4.38 |
| Hydroxylamine, O-(2-methylpropyl)- | -19.87 | -4.79 | -19.56 | -5.65 | -3.73 | -3.98 | -4.25 | -3.91 | -19.65 |
| Methyl methacrylate | -4.99 | -3.38 | -3.52 | -2.42 | -3.44 | -3.71 | -3.74 | -3.63 | -3.53 |
| 1,3,5-Cycloheptatriene | -2.80 | -3.39 | -3.38 | -3.32 | -3.52 | -2.21 | -2.88 | -2.84 | -3.95 |
| 4-Ethylbenzamide | -2.40 | -2.31 | -1.72 | -2.37 | -2.69 | -1.58 | -3.26 | -1.75 | -2.14 |
| Hexanal | -2.40 | -1.32 | -2.76 | 18.95 | -0.93 | -2.97 | -5.76 | -3.04 | -3.70 |
| Hexane, 2,3,4-trimethyl- | -1.52 | -2.49 | -1.88 | -2.12 | -1.89 | -2.12 | -1.36 | -2.39 | -2.22 |
| Methoxyacetic acid, hexyl ester | -1.93 | -2.53 | -2.11 | -2.29 | -1.99 | -2.47 | -1.06 | -19.42 | -2.38 |
| p-Xylene + 6.4320683 | -2.36 | -3.24 | -2.46 | -4.64 | -4.27 | -3.77 | -2.29 | -19.42 | -3.02 |
| 1,3-Cyclopentadiene, 5-(1-methylethylidene)- | -19.87 | -1.75 | -19.56 | -4.53 | -18.97 | -20.20 | -5.14 | -4.32 | -19.65 |
| Acetic acid, 2-phenylethyl ester + 7.1055326 | -5.10 | -5.39 | -4.09 | -4.58 | -4.02 | -3.75 | -3.15 | -4.49 | -19.65 |
| Cyclohexanone | -3.46 | -3.68 | -4.90 | -3.50 | -18.97 | -20.20 | -20.23 | -19.42 | -19.65 |
| Bicyclo[3.1.0]hex-2-ene, 4-methyl-1-(1-methylethyl)- | -19.87 | -4.41 | -4.27 | -4.61 | -18.97 | -3.55 | -4.61 | -4.10 | -4.52 |
| Pentane, 2,2,3-trimethyl- | -19.87 | -19.20 | -3.18 | -3.92 | -18.97 | -2.50 | -20.23 | -3.17 | -3.09 |
| Pentane, 2,2,3,4-tetramethyl- + 9.821276 | -19.87 | -4.71 | -4.55 | -5.04 | -4.85 | -3.64 | -4.92 | -19.42 | -4.90 |
| Hexane, 1-chloro- | -3.77 | -19.20 | -19.56 | -18.95 | -4.68 | -4.02 | -3.37 | -4.88 | -4.62 |
| Heptane, 2,2,4,6,6-pentamethyl- | -2.64 | -1.96 | -1.73 | -2.64 | -18.97 | -1.16 | -1.98 | -1.97 | -2.11 |
| Cyclohexene, 1-methyl-4-(1-methylethenyl)-, (S)- | -2.21 | -19.20 | -2.77 | -0.94 | -1.55 | -2.85 | -1.04 | -19.42 | -2.42 |
| 1-Hexanol, 2-ethyl- | 0.57 | 0.77 | 0.49 | 1.13 | 1.35 | -0.31 | 0.32 | 0.48 | 0.70 |
| 1-Nonene, 4,6,8-trimethyl- | -1.53 | -0.85 | -0.67 | -1.17 | -1.21 | -0.25 | -1.33 | -0.90 | -1.00 |
| Decane, 2,5,9-trimethyl- | -4.11 | -3.11 | -3.04 | -3.46 | -3.46 | -2.82 | -20.23 | -3.28 | -3.29 |
| Pentane, 2,2,3,4-tetramethyl- | -2.17 | -1.46 | -1.22 | -2.11 | -2.06 | -0.58 | -3.21 | -1.49 | -1.59 |
| Hexane, 2,3,4-trimethyl- + 12.597675 | -1.64 | -2.87 | -1.40 | -1.76 | -1.73 | -2.06 | -1.70 | -1.90 | -1.74 |
| Oxalic acid, allyl nonyl ester | -3.33 | -3.41 | -2.93 | -3.48 | -18.97 | -20.20 | -3.12 | -3.46 | -19.65 |
| Hexane, 2,2,3-trimethyl- | -2.29 | -1.62 | -1.41 | -2.71 | -2.11 | -0.94 | -2.30 | -1.69 | -1.69 |
| Pentane, 2,2,3,4-tetramethyl- + 13.338136 | -3.30 | -2.90 | -19.56 | -18.95 | -3.87 | -20.20 | -3.73 | -2.82 | -5.54 |
| Octane, 3,5-dimethyl- | -1.38 | -1.69 | -1.28 | -1.58 | -1.61 | -1.57 | -1.56 | -4.12 | -1.49 |
| 2-Nonen-1-ol, (E)- | -0.61 | -19.20 | -0.73 | -0.96 | -1.11 | -1.15 | -0.76 | -1.15 | -0.74 |
| Hexane, 3-methyl- | -4.03 | -4.14 | -4.97 | -4.51 | -18.97 | -3.80 | -4.10 | -4.18 | -3.74 |
| Propanoic acid, 2-hydroxy-, pentyl ester | -4.48 | -19.20 | -3.86 | -4.72 | -18.97 | -4.32 | -4.64 | -4.14 | -4.67 |
| Octane, 3,5-dimethyl- + 17.273 | -1.98 | -3.10 | -3.01 | -2.89 | -18.97 | -2.29 | -2.67 | -3.04 | -2.75 |
| 2,3-Epoxyhexanol | -3.40 | -3.82 | -3.48 | -4.35 | -4.66 | -3.29 | -3.79 | -4.95 | -3.41 |
| Hexane, 2,3,4-trimethyl- + 19.489073 | -3.04 | -3.68 | -2.87 | -18.95 | -3.39 | -3.34 | -2.64 | -19.42 | -3.48 |
| Hexane, 2,4-dimethyl- | -3.02 | -19.20 | -4.07 | -18.95 | -3.93 | -3.46 | -3.30 | -4.22 | -3.67 |
| Hexane, 2,3,4-trimethyl- + 20.846872 | -19.87 | -19.20 | -2.94 | -3.44 | -18.97 | -3.46 | -2.63 | -3.94 | -3.71 |

| | Malaria Positive | | | | | | | |
|---|---|---|---|---|---|---|---|---|
| Compound Annotation | Patient 28 | Patient 29 | Patient 30 | Patient 31 | Patient 32 | Patient 33 | Patient 34 | Patient 35 |
| Formamide | -21.17 | -20.35 | -3.63 | -1.32 | -2.19 | -2.34 | -2.49 | -3.73 |
| Isopropyl Alcohol | -21.17 | -20.35 | -0.63 | 2.05 | -0.45 | 0.22 | 0.28 | -1.16 |
| Acetone | 4.00 | 1.34 | 3.99 | 5.58 | 2.96 | 4.94 | 4.83 | 2.45 |
| Cyclopropane, ethylidene- | -21.17 | -20.35 | 0.14 | -19.53 | 0.91 | 0.80 | -2.01 | -1.60 |
| 2-Propanol, 1,3-dichloro- | -2.39 | -1.31 | -19.18 | 0.49 | 0.20 | 0.47 | 0.36 | 1.11 |
| 1,3-Hexadien-5-yne | -3.08 | -4.05 | -2.38 | -2.07 | -3.27 | -3.50 | -2.71 | -2.12 |
| O-Butylisourea | -21.17 | -3.53 | -19.18 | -1.93 | -2.50 | -2.31 | -19.62 | -1.92 |
| 2-Butanone, 3-methyl- | -3.35 | -4.00 | -3.33 | -2.17 | -19.23 | -3.37 | -2.88 | -3.32 |
| Hydroxylamine, O-(2-methylpropyl)- | -4.80 | -4.61 | -19.18 | -3.17 | -19.23 | -4.51 | -4.85 | -3.54 |
| Methyl methacrylate | -4.19 | -4.24 | -2.99 | -3.49 | -2.86 | -3.48 | -3.65 | -3.15 |
| 1,3,5-Cycloheptatriene | -2.47 | -3.26 | -3.46 | -2.19 | -3.25 | -2.95 | -3.55 | -1.51 |
| 4-Ethylbenzamide | -2.70 | -2.72 | -1.88 | -1.40 | -1.94 | -1.86 | -2.11 | -1.63 |
| Hexanal | -21.17 | -2.54 | -19.18 | -3.42 | -3.99 | -3.63 | -3.44 | -2.65 |
| Hexane, 2,3,4-trimethyl- | -2.24 | -2.36 | -2.38 | -3.10 | -1.99 | -2.08 | -1.92 | -1.70 |
| Methoxyacetic acid, hexyl ester | -2.39 | -1.54 | -1.98 | -19.53 | -2.11 | -19.21 | -1.89 | -1.94 |
| p-Xylene + 6.4320683 | -5.80 | -4.14 | -5.28 | -19.53 | -19.23 | -3.07 | -2.27 | -2.25 |
| 1,3-Cyclopentadiene, 5-(1-methylethylidene)- | -2.84 | 0.37 | -1.70 | -1.59 | -3.63 | -19.21 | -3.91 | -1.41 |
| Acetic acid, 2-phenylethyl ester + 7.1055326 | -4.28 | -3.28 | -4.80 | -4.20 | -4.52 | -19.21 | -3.97 | -19.07 |
| Cyclohexanone | -4.21 | -3.85 | -19.18 | -4.01 | -19.23 | -19.21 | -19.62 | -3.16 |
| Bicyclo[3.1.0]hex-2-ene, 4-methyl-1-(1-methylethyl)- | -4.74 | -4.71 | -3.26 | -4.29 | -3.95 | -4.62 | -4.32 | -4.14 |

-continued

| | | | | | | | | |
|---|---|---|---|---|---|---|---|---|
| Pentane, 2,2,3-trimethyl- | −4.02 | −3.62 | −3.06 | −2.73 | −3.58 | −3.77 | −19.62 | −3.16 |
| Pentane, 2,2,3,4-tetramethyl- + 9.821276 | −5.08 | −20.35 | −4.49 | −4.73 | −4.76 | −4.89 | −4.34 | −4.44 |
| Hexane, 1-chloro- | −4.09 | −3.95 | −4.30 | −4.04 | −19.23 | −5.22 | −4.22 | −3.77 |
| Heptane, 2,2,4,6,6-pentamethyl- | −3.03 | −2.36 | −1.89 | −1.20 | −2.48 | −19.21 | −1.58 | −1.89 |
| Cyclohexene, 1-methyl-4-(1-methylethenyl)-, (S)- | −2.26 | −1.10 | −1.97 | −19.53 | −1.11 | −1.49 | −2.54 | −1.71 |
| 1-Hexanol, 2-ethyl- | −0.01 | 0.20 | 0.64 | −0.48 | 0.82 | 0.59 | 0.77 | 1.30 |
| 1-Nonene, 4,6,8-trimethyl- | −1.71 | −1.54 | −0.80 | −0.44 | −1.22 | −1.29 | −0.54 | −0.66 |
| Decane, 2,5,9-trimethyl- | −3.94 | −3.90 | −19.18 | −19.53 | −19.23 | −3.69 | −2.80 | −3.09 |
| Pentane, 2,2,3,4-tetramethyl- | −2.52 | −2.22 | −1.52 | −0.70 | −2.06 | −4.91 | −1.07 | −1.45 |
| Hexane, 2,3,4-trimethyl- + 12.597675 | −2.37 | −1.91 | −1.14 | −2.22 | −1.71 | −2.02 | −1.40 | −1.39 |
| Oxalic acid, allyl nonyl ester | −4.06 | −3.49 | −19.18 | −3.30 | −3.41 | −19.21 | −19.62 | −3.07 |
| Hexane, 2,2,3-trimethyl- | −2.78 | −2.60 | −1.85 | −1.01 | −2.41 | −3.77 | −1.26 | −1.58 |
| Pentane, 2,2,3,4-tetramethyl- + 13.338136 | −6.13 | −3.77 | −3.18 | −2.06 | −3.91 | −19.21 | −19.62 | −19.07 |
| Octane, 3,5-dimethyl- | −2.23 | −1.76 | −1.18 | −1.92 | −1.55 | −19.21 | −1.12 | −1.20 |
| 2-Nonen-1-ol, (E)- | −1.25 | −0.69 | −19.18 | −1.48 | −19.23 | −19.21 | −0.59 | −0.45 |
| Hexane, 3-methyl- | −4.82 | −4.44 | −3.90 | −4.01 | −4.41 | −4.47 | −5.35 | −3.93 |
| Propanoic acid, 2-hydroxy-, pentyl ester | −4.42 | −20.35 | −4.74 | −4.42 | −19.23 | −5.12 | −19.62 | −4.21 |
| Octane, 3,5-dimethyl + 17.273 | −2.80 | −3.02 | −2.70 | −2.75 | −19.23 | −2.71 | −19.62 | −2.31 |
| 2,3-Epoxyhexanol | −3.26 | −3.99 | −3.95 | −3.56 | −3.20 | −3.85 | −3.93 | −3.72 |
| Hexane, 2,3,4-trimethyl- + 19.489073 | −3.64 | −3.14 | −2.51 | −3.93 | −3.34 | −19.21 | −19.62 | −2.59 |
| Hexane, 2,4-dimethyl- | −3.78 | −3.74 | −3.59 | −4.20 | −3.74 | −3.61 | −19.62 | −3.33 |
| Hexane, 2,3,4-trimethyl- + 20.846872 | −3.56 | −3.25 | −19.18 | −4.25 | −19.23 | −3.53 | −19.62 | −2.66 |

Example 4

Diagnosis of Malaria in Patient Samples Using Six VOCs

Using the data and methods described above in Examples 1-3, the accuracy of using a "breathprint" based on abundance signatures of the 6 VOCs identified in Example 3 to diagnose malaria in one Malawian cohort (Cohort 1) was determined. FIG. 4A depicts a schema summarizing the analytical process described partially above. In brief, a standardized GC/MS spectrum from a patient's breath sample was logarithmically transformed (compressed) to yield an abundance heat map which was correlated to malaria diagnosis to yield a linear classification of diagnosis.

FIG. 4B shows the logarithmic compression of a representative spectrum with the peaks for the 6 compounds of interest identified with red numbers. A color bar below the compressed spectrum visually depicts the abundance of each peak. Three of the compounds were positively identified as nonanal, isoprene and tridecane by comparison to true standards obtained from Sigma Aldrich and Supelco. The remaining three (4-methyl undecane, 3,7-dimethyl decane and 2,3,4-trimethyl hexane) were annotated through manually curated reference to a spectral library. The isolated spectra of the annotated compounds from patient samples are depicted in FIG. 5 and the chemical characteristics of all six VOCs are described in Table 4 below.

TABLE 4

| Compound Name | Structure | Base Ion (m/z) | Retention Time (min) | Retention Index[1] |
|---|---|---|---|---|
| 4-methylundecane | 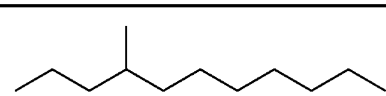 | 43 | 14.52 | 1113 |
| Nonanal[2] | 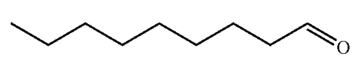 | 57 | 14.25 | 1104 |
| Isoprene[2] | 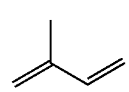 | 67 | 1.50 | 520 (lit.) |
| Tridecane[2] | 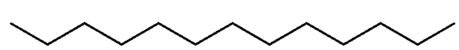 | 57 | 20.26 | 1300 |
| 3,7-dimethyldecane | 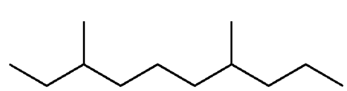 | 57 | 11.83 | 1031 |

TABLE 4-continued

| Compound Name | Structure | Base Ion (m/z) | Retention Time (min) | Retention Index[1] |
|---|---|---|---|---|
| 2,3,4-trimethylhexane | 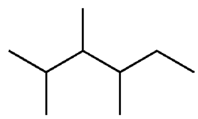 | 43 | 6.27 | 860 |

[1] Calculated using definition of Van Den Dool and Kratz (J. Chromatogr. 1963; 11: 463-71).
[2] Identity of these compounds were confirmed by reference to a true standard.

FIG. 4C shows a heat map of the z-scores of the 6 identified VOCs in each patient. Each row is a single patient separated into malaria negative (top) and malaria positive (bottom) groups. Each column is the abundance (z-score) of each of the 6 VOCs (labeled on the x-axis). Red denotes low abundance relative to mean abundance across all samples (negative z-score) and purple denotes high abundance relative to mean abundance across all samples (positive z-score). This data is presented in tabular form below. Each compound either was found to have a lower or higher concentration in malaria positive individuals compared to controls. VOCs with lowered abundance included methyl undecane, nonanal, isoprene, and tridecane. VOCs with elevated abundance included dimethyl decane and trimethyl hexane.

| Patient | | Nonanal | Isoprene | Tridecane | Trimethyl hexane | Dimethyl decane | Methyl undecane |
|---|---|---|---|---|---|---|---|
| Malaria Negative | 1 | −0.009 | 0.237 | 0.178 | 0.214 | −1.162 | 0.397 |
| | 2 | 0.397 | 0.599 | 0.390 | 0.232 | −0.626 | 0.506 |
| | 3 | 0.303 | 0.542 | 0.256 | 0.193 | −0.299 | 0.411 |
| | 4 | 0.327 | 0.306 | 0.167 | 0.123 | 0.595 | 0.567 |
| | 5 | 0.262 | 0.347 | 0.208 | 0.181 | −1.278 | −1.963 |
| | 6 | 0.310 | 0.231 | 0.272 | 0.196 | −0.822 | −1.963 |
| | 7 | 0.363 | 0.628 | 0.323 | 0.371 | 0.296 | −1.963 |
| | 8 | 0.397 | 0.063 | 0.458 | 0.273 | 0.188 | 0.607 |
| | 9 | 0.351 | 0.598 | 0.341 | 0.309 | −0.128 | 0.559 |
| | 10 | 0.299 | 0.557 | 0.157 | 0.162 | −0.672 | 0.386 |
| | 11 | 0.399 | 0.385 | 0.447 | 0.270 | −0.477 | 0.468 |
| | 12 | 0.335 | 0.549 | 0.280 | 0.392 | −0.039 | −1.963 |
| | 13 | 0.436 | 0.687 | 0.388 | 0.447 | −0.154 | 0.507 |
| | 14 | 0.431 | 0.546 | 0.413 | 0.085 | −0.974 | 0.467 |
| | 15 | 0.266 | 0.489 | 0.190 | 0.261 | −1.339 | −1.963 |
| | 16 | 0.333 | 0.610 | 0.236 | 0.328 | 0.266 | 0.491 |
| | 17 | 0.415 | −2.143 | 0.374 | 0.805 | 0.458 | 0.285 |
| | 18 | 0.429 | 0.438 | 0.355 | 0.399 | 0.783 | −1.963 |
| Malaria Positive | 19 | 0.443 | 0.589 | 0.482 | 0.371 | −0.238 | 0.584 |
| | 20 | −2.730 | 0.186 | −3.194 | 0.119 | −0.199 | 0.459 |
| | 21 | 0.374 | 0.472 | 0.185 | 0.276 | 0.888 | 0.384 |
| | 22 | 0.234 | 0.378 | −3.194 | 0.117 | −1.356 | 0.358 |
| | 23 | 0.215 | 0.350 | 0.088 | 0.183 | −1.385 | −1.963 |
| | 24 | 0.409 | −2.143 | 0.458 | 0.330 | 3.052 | 0.674 |
| | 25 | 0.479 | −2.143 | 0.499 | 0.616 | 0.909 | 0.631 |
| | 26 | 0.281 | 0.423 | 0.123 | −3.182 | 0.146 | 0.488 |
| | 27 | 0.387 | 0.269 | 0.293 | 0.240 | 0.415 | 0.596 |
| | 28 | 0.554 | −2.143 | 0.599 | 0.537 | 2.054 | 0.667 |
| | 29 | 0.510 | −2.143 | 0.429 | 0.543 | 0.729 | 0.595 |
| | 30 | −2.730 | 0.531 | 0.207 | 0.225 | −0.155 | 0.493 |
| | 31 | 0.246 | −2.143 | 0.152 | −3.182 | 1.308 | 0.533 |
| | 32 | −2.730 | 0.646 | 0.187 | 0.209 | −0.890 | 0.420 |
| | 33 | −2.730 | 0.628 | 0.209 | −3.182 | −1.074 | 0.407 |
| | 34 | 0.406 | 0.295 | −3.194 | 0.330 | 1.270 | 0.332 |
| | 35 | 0.338 | 0.276 | 0.239 | 0.211 | −0.091 | 0.470 |

FIG. 4D is a graphical schematic of the cumulative abundance metric used to classify individuals as malaria positive or negative. The abundance values for the six VOCs were linearly combined to create a cumulative abundance metric with the caveat that negatively correlated VOCs were subtracted rather than added. The cumulative abundance measurements for each sample are graphically depicted in FIGS. 4E and 4F. In FIG. 4E cumulative abundances are depicted in a histogram with each bar colored to represent malaria (+) (red) or malaria (−) (blue) individuals. From these histograms, Gaussian distributions (overlaid curves) were generated to determine a threshold level for positive diagnosis (black vertical line). In FIG. 4F, the same data is depicted as a scatterplot of patient vs. cumulative abundance. As in FIG. 4C, the points on the top half of the scatterplot correspond to malaria negative individuals (blue) and those on the bottom half correspond to malaria positive individuals (red). A clear separation between classes is apparent in this representation. The threshold line in FIG. 4F is reproduced from that in FIG. 4E.

Using the cumulative abundance of the six identified VOCs, patient samples were classified as malaria positive or negative. Each patient was classified using the nearest mean classification scheme, described earlier, based on a model using all patients. FIG. 4G shows a confusion matrix of actual and predicted malaria infection status with the percentage of patients in each class displayed. 83% of the classifications were correct with a specificity of 94% and a sensitivity of 71%.

Therefore, this example shows the feasibility and improvement of using a cumulative abundance metric of multiple terpenes to accurately diagnose malaria in a pediatric population.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

In view of the above, it will be seen that the several objects of the invention are achieved and other advantageous results attained.

As various changes could be made in the above methods without departing from the scope of the invention, it is intended that all matter contained in the above description and shown in the accompanying drawings shall be interpreted as illustrative and not in a limiting sense.

What is claimed is:

1. A method for monitoring a subject with a *Plasmodium* parasite infection (malaria), the method comprising:
   analyzing a sample of exhaled breath or condensate breath obtained from the subject for a series of volatile organic compounds (VOCs) comprising:

(1) isoprene,
(2) nonanal,
(3) tridecane,
(4) 4-methyl undecane,
(5) 3,7-dimethyl decane, and
(6) 2,3,4-trimethyl hexane;
determining a concentration for each of the VOCs; and
calculating a cumulative abundance based on the concentrations for the VOCs, wherein the cumulative abundance indicates a *Plasmodium* parasite infection.

2. The method of claim 1 wherein the analysis of the series of VOCs comprises the use of at least one technique selected from the group consisting of photo ionization detection, flame ionization detection, gas chromatography-mass spectrometry (GC-MS), proton transfer reaction mass spectrometry (PTR-MS), colorimetry, infrared spectroscopy, electrochemical fuel cell sensing, semiconductor gas sensing, quartz tuning fork (QTF) sensors, electronic noses and combinations thereof.

3. The method of claim 1 wherein the analysis of the series of VOCs comprises is conducted using a portable, hand-held breathalyzer device.

4. A method of detecting a series of volatile organic compounds (VOCs) in a subject, the method comprising analyzing a sample of exhaled breath or condensate breath obtained from the subject for the series of VOCs comprising:
(1) isoprene,
(2) nonanal,
(3) tridecane,
(4) 4-methyl undecane,
(5) 3,7-dimethyl decane, and
(6) 2,3,4-trimethyl hexane; and
determining a concentration for each of the VOCs.

5. The method of claim 1 wherein the sample is exhaled breath.

6. The method of claim 1 wherein the *Plasmodium* parasite infection is an infection of *Plasmodium falciparum* or *Plasmodium vivax*.

7. The method of claim 1 further comprising condensing or concentrating the sample before analysis.

8. The method of claim 1 wherein the subject is a human.

* * * * *